United States Patent
Mitsuya et al.

(10) Patent No.: US 10,933,067 B2
(45) Date of Patent: Mar. 2, 2021

(54) NUCLEOSIDE DERIVATIVE HAVING PHYSIOLOGICAL ACTIVITY SUCH AS ANTIVIRAL ACTIVITY

(71) Applicant: NATIONAL CENTER FOR GLOBAL HEALTH AND MEDICINE, Tokyo (JP)

(72) Inventors: Hiroaki Mitsuya, Tokyo (JP); Hiroki Kumamoto, Tokyo (JP)

(73) Assignee: NATIONAL CENTER FOR GLOBAL HEALTH AND MEDICINE, Tokyo (JP)

( * ) Notice: Subject to any disclaimer, the term of this patent is extended or adjusted under 35 U.S.C. 154(b) by 0 days.

(21) Appl. No.: 16/349,832

(22) PCT Filed: Nov. 13, 2017

(86) PCT No.: PCT/JP2017/040790
§ 371 (c)(1),
(2) Date: May 14, 2019

(87) PCT Pub. No.: WO2018/092728
PCT Pub. Date: May 24, 2018

(65) Prior Publication Data
US 2019/0275050 A1    Sep. 12, 2019

(30) Foreign Application Priority Data
Nov. 16, 2016 (JP) .............................. JP2016-223511

(51) Int. Cl.
| | |
|---|---|
| *A61K 31/522* | (2006.01) |
| *C07D 487/04* | (2006.01) |
| *A61P 31/20* | (2006.01) |
| *A61P 31/18* | (2006.01) |
| *A61P 31/12* | (2006.01) |

(52) U.S. Cl.
CPC ............ *A61K 31/522* (2013.01); *A61P 31/12* (2018.01); *A61P 31/18* (2018.01); *A61P 31/20* (2018.01); *C07D 487/04* (2013.01)

(58) Field of Classification Search
CPC ........................... A61K 31/522; C07D 487/04
See application file for complete search history.

(56) References Cited

U.S. PATENT DOCUMENTS

| 5,627,160 A | 5/1997 | Lin et al. |
|---|---|---|
| 2002/0022722 A1 | 2/2002 | Ohrui et al. |
| 2005/0080034 A1 | 4/2005 | Standring et al. |
| 2005/0215512 A1 | 9/2005 | Kohgo et al. |
| 2009/0318380 A1 | 12/2009 | Sofia et al. |
| 2011/0244027 A1 | 10/2011 | Chu et al. |
| 2016/0280729 A1 | 9/2016 | Moussa et al. |

FOREIGN PATENT DOCUMENTS

| JP | H4-282373 A | 10/1992 |
|---|---|---|
| JP | H06-80688 A | 3/1994 |
| JP | 2001-335592 A | 12/2001 |
| JP | 2001-335593 A | 12/2001 |
| JP | 2004-107329 A | 4/2004 |
| JP | 2004-244422 A | 9/2004 |
| JP | 2008-273960 A | 11/2008 |
| JP | 2011-503234 A | 1/2011 |
| JP | 2013-510904 A | 3/2013 |
| WO | 2003/068796 A1 | 8/2003 |
| WO | 2005/090349 A1 | 9/2005 |
| WO | 2015/077360 A2 | 5/2015 |
| WO | 2016/134054 A1 | 8/2016 |

OTHER PUBLICATIONS

European Extended Search Report dated Jun. 16, 2020 in European Patent Application No. 17871309.5.
Higashi-Kuwata et al., "CMCdG, a Novel Nucleoside Analog with Favorable Safety Features, Exerts Potent Activity Against Wild-Type and Entecavir-Resistant Hepatitis B Virus," Antimicrobial Agents and Chemotherapy, vol. 63, No. 4, Apr. 2019, pp. 1-17.
Kodama, El-Ichi et al. "4'-Ethynyl Nucleoside Analogs: Potent Inhibitors of Multidrug-Resistant Human Immunodeficiency Virus Variants In Vitro". Antimicrobial Agents and Chemotherapy, vol. 45, pp. 1539-1546, 2001.
Kumamoto, Hiroki et al. "Diastereoselective Synthesis of 6"-(Z)- and 6"-(E)-Fluoro Analogues of Anti-hepatitis B Virus Agent Entecavir and its Evaluation of the Activity and Toxicity Profile of the Diastereomers". The Journal of Organic Chemistry, vol. 81, pp. 2827-2836, 2016.

(Continued)

*Primary Examiner* — Yong S. Chong
(74) *Attorney, Agent, or Firm* — Oliff PLC

(57) ABSTRACT

It is found that a nucleoside derivative represented by the following general formula (1) has an anti-viral activity and is less toxic to host cells.

[Chem. 1]

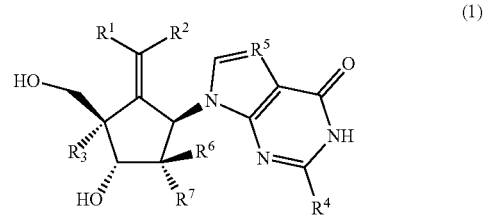

(1)

[in the formula, $R^1$ represents a hydrogen or halogen atom, $R^2$ represents a hydrogen or halogen atom, $R^3$ represents a cyano group, an alkyl group which may have a substituent, an alkenyl group which may have a substituent, an alkynyl group which may have a substituent, a halogen atom, or an azido group, $R^4$ represents an amino group, a hydrogen atom, a halogen atom, or a hydroxy group, $R^5$ represents a nitrogen atom or a methine group, $R^6$ represents a hydrogen atom or a hydroxy group, and $R^7$ represents a hydrogen atom or a hydroxy group].

5 Claims, No Drawings

(56) References Cited

OTHER PUBLICATIONS

Ohrui, Hiroshi. Japan Society for Bioscience, Biotechnology, and Agrochemistry, vol. 44, pp. 660-662, 2006.
Takamatsu, Yuki et al. "4'-Modified Nucleoside Analogs: Potent Inhibitors Active Against Entecavir-Resistant Hepatitis B Virus". Hepatology, vol. 62, pp. 1024-1036, 2015.
Feb. 13, 2018 International Search Report issued in International Patent Application No. PCT/JP2017/040790.

NUCLEOSIDE DERIVATIVE HAVING PHYSIOLOGICAL ACTIVITY SUCH AS ANTIVIRAL ACTIVITY

TECHNICAL FIELD

The present invention relates to a nucleoside derivative exhibiting an antiviral activity, and an antiviral agent containing the derivative as an active ingredient.

BACKGROUND ART

When one is infected with hepatitis B virus (HBV), hepatitis may occur acutely or fulminantly, resulting in death in worst cases. Instead, chronic hepatitis occurs, and progresses to liver cirrhosis and then hepatocellular carcinoma in some cases. The number of patients infected with HBV is estimated at about 260 million in the whole world. The prevalence rate is very high especially in Southeast Asia, and there is a global demand for the development of effective therapeutic methods for HBV.

The HBV is an incomplete double-stranded DNA virus and is known to conduct reverse transcription in which DNA is synthesized from RNA in the life cycle of HBV. Meanwhile, the human, who may become a host, does not conduct reverse transcription. Hence, if the reverse transcription in this stage is inhibited, only HBV replication can be inhibited. From these viewpoints, nucleoside derivative preparations have been developed as therapeutic agents for the HBV infection (PTLs 1 and 2).

Similarly, AIDS is an infectious disease for which the development of effective therapies is strongly demanded worldwide. Human immunodeficiency virus (HIV) causing AIDS is also replicated by reverse transcription. For this reason, many nucleoside derivative preparations which inhibit HIV replication have been developed (PTLs 3 to 7).

CITATION LIST

Patent Literature

[PTL 1] Japanese Unexamined Patent Application Publication No. 2004-244422
[PTL 2] Japanese Unexamined Patent Application Publication No. 2008-273960
[PTL 3] Japanese Unexamined Patent Application Publication No. 2001-335592
[PTL 4] Japanese Unexamined Patent Application Publication No. 2001-335593
[PTL 5] International Publication No. WO2003/068796
[PTL 6] Japanese Unexamined Patent Application Publication No. 2004-107329
[PTL 7] International Publication No. WO2005/090349

SUMMARY OF INVENTION

Technical Problem

Many of the current nucleoside derivative preparations are toxic to host cells, that is, cells of humans who take the preparations, and entail a problem of side effects due to medication for medium and long terms. In addition, resistant strains to nucleoside derivatives may be produced for a dosing period. Therefore, in the current situation, effective therapies against infections with viruses such as HBV have not been established.

The present invention has been made in view of these circumstances, and has an objective to provide a nucleoside derivative having an antiviral activity and having low toxicity to host cells.

Solution to Problem

As a result of earnest and intensive studies to solve the aforementioned problems, the present inventors have found that a compound which is a nucleoside derivative represented by the following general formula (1) where $R^1$ and $R^2$ are fluorine and hydrogen, $R^3$ is a cyano group, $R^4$ is an amino group, $R^5$ is nitrogen, and $R^6$ and $R^7$ are both hydrogen is capable of exhibiting an excellent antiviral activity against HBV, and further exhibiting an antiviral activity against entecavir-resistant HBV. In addition, the compound also exhibited an antiviral activity against HIV. On the other hand, it has been also found that the compound has low cytotoxicity to cells hosting the virus.

Moreover, as similar to the above, it has been also found that a compound which is a nucleoside derivative represented by the following general formula (1) where $R^1$ and $R^2$ are both hydrogen, $R^3$ is a cyano group, a methyl group, a monofluoromethyl group, an ethenyl group, or an ethynyl group, $R^4$ is an amino group, $R^5$ is nitrogen, and $R^6$ and $R^7$ are both hydrogen is capable of exhibiting an excellent antiviral activity and has low cytotoxicity to cells hosting the virus. As a result, the present invention has been completed.

[Chem. 1]

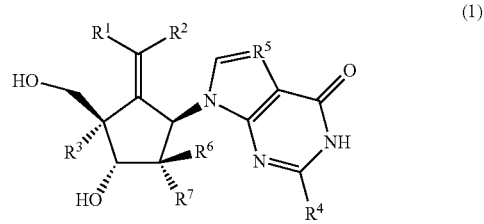

(1)

Specifically, the present invention relates to a nucleoside derivative having an antiviral activity, and an antiviral agent containing the derivative as an active ingredient, and more specifically provides the followings.
<1> A nucleoside derivative represented by the above general formula (1).
[In the formula, $R^1$ represents a hydrogen atom or a halogen atom. $R^2$ represents a hydrogen atom or a halogen atom. $R^3$ represents a cyano group, an alkyl group which may have a substituent, an alkenyl group which may have a substituent, an alkynyl group which may have a substituent, a halogen atom, or an azido group. $R^4$ represents an amino group, a hydrogen atom, a halogen atom, or a hydroxy group. $R^5$ represents a nitrogen atom or a methine group. $R^6$ represents a hydrogen atom or a hydroxy group. $R^7$ represents a hydrogen atom or a hydroxy group.]
<2> An antiviral agent comprising the nucleoside derivative according to <1> as an active ingredient.
<3> The antiviral agent according to <2>, which is an anti-hepatitis B virus agent.
<4> The antiviral agent according to <2>, which is an anti-human immunodeficiency virus agent.

Advantageous Effects of Invention

According to the present invention, it is possible to provide a nucleoside derivative having an antiviral activity against HIV, HBV, and soon, and having low toxicity to host cells. In addition, it is also possible to provide a nucleoside derivative capable of exhibiting an antiviral activity against even HBV resistant to the existing nucleoside derivative (such as entecavir).

DESCRIPTION OF EMBODIMENTS (Nucleoside Derivative) As demonstrated in Examples described later, nucleoside derivatives represented by the following formula were found having an antiviral activity against the hepatitis B virus (HBV) or the human immunodeficiency virus (HIV). Thus, the present invention provides nucleoside derivatives represented by the following general formula (1) and having the antiviral activity.

[Chem. 2]

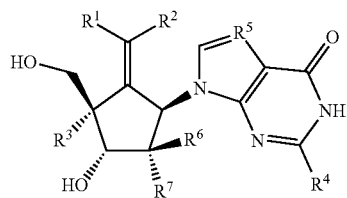

In the formula, $R^1$ represents a hydrogen atom or a halogen atom. $R^2$ represents a hydrogen atom or a halogen atom. $R^3$ represents a cyano group, an alkyl group which may have a substituent, an alkenyl group which may have a substituent, an alkynyl group which may have a substituent, a halogen atom, or an azido group. $R^4$ represents an amino group, a hydrogen atom, a halogen atom, or a hydroxy group. $R^5$ represents a nitrogen atom or a methine group. $R^6$ represents a hydrogen atom or a hydroxy group. $R^7$ represents a hydrogen atom or a hydroxy group.

In the present invention, the "antiviral activity" means an activity in cells (host cells) infected with a virus such as HBV to eliminate the virus or suppress the proliferation of the virus, and an example thereof is an activity to suppress virus replication in host cells. This activity can be evaluated by using an $EC_{50}$ value calculated with the number of viruses replicated in the host cells or the like as an index. For example, the anti-HIV activity and the anti-HBV activity can be evaluated based on measurement values obtained one week after or two weeks after the administration of each test compound in accordance with methods described in Test Examples 1 to 3. The nucleoside derivative of the present invention has an $EC_{50}$ value of the antiviral activity of preferably 0.2 μM or less, more preferably 0.1 μM or less, more preferably 0.07 μM or less, even more preferably 0.05 μM or less, more preferably 0.02 μM or less, even more preferably 0.01 μM or less, and more preferably 0.005 μM or less (for example, 0.004 μM or less, 0.003 μM or less, 0.002 μM or less, or 0.001 μM or less). Also, the nucleoside derivative of the present invention may be used to exhibit the antiviral activity against any target, not particularly limited, and may target a virus having a reverse transcriptase (EC 2.7.7.49), which may be a RNA virus or a DNA virus. It is preferable to target HIV and HBV.

As the HBV, there are known genotypes of A (A2/Ae, A1/Aa), B (Ba, B1/Bj), C (Cs, Ce), D to H and J. The nucleoside derivative of the present invention only has to have an antiviral activity against at least one genotype of HBV. Among the above genotypes, HBV/Ce is known to be a genotype that exhibits the resistance to the existing nucleoside derivative preparation named entecavir. Therefore, the nucleoside derivative of the present invention is preferably a nucleoside derivative having an antiviral activity against HBV/Ce.

In addition, it is preferable that the nucleoside derivative of the present invention have low cytotoxicity. In the present invention, the "cytotoxicity" means an activity of killing a cell, inhibiting its function, or suppressing its proliferation. Such activity can be evaluated by using a $CC_{50}$ value calculated using the number of live cells or the like as an index as demonstrated in Examples described later. The nucleoside derivative of the present invention has a $CC_{50}$ value of preferably 10 μM or more, more preferably 50 μM or more, and further preferably 100 μM or more.

In the nucleoside derivative of the present invention, the alkyl group in the "alkyl group which may have a substituent" is not particularly limited, but is preferably a linear, branched or cyclic alkyl group having 1 to 6 carbon atoms, more preferably a methyl group or an ethyl group, and further preferably a methyl group. The substituent in the "alkyl group which may have a substituent" is not particularly limited, and examples thereof are a hydroxy group, a halogen atom, an alkoxy group, a cyano group, and an amino group. Preferable ones are a hydroxy group and a halogen atom (more preferably a fluorine atom). More specifically, the "alkyl group which may have a substituent" is preferably a monofluoromethyl group or a hydroxymethyl group.

The alkenyl group in the "alkenyl group which may have a substituent" is not particularly limited, but is preferably a linear, branched, or cyclic alkenyl group having 2 or more carbon atoms, more preferably a linear, branched, or cyclic alkenyl group having 2 to 6 carbon atoms, and further preferably an ethenyl group. The substituent in the "alkenyl group which may have a substituent" is not particularly limited, and examples thereof are a halogen atom, a hydroxy group, an alkoxy group, a cyano group, and an amino group.

The alkynyl group in the "alkynyl group which may have a substituent" is not particularly limited, but is preferably a linear, branched, or cyclic alkynyl group having 2 or more carbon atoms, more preferably a linear, branched, or cyclic alkynyl group having 2 to 6 carbon atoms, and further preferably an ethynyl group. The substituent in the "alkynyl group which may have a substituent" is not particularly limited, and examples thereof are a halogen atom, a hydroxy group, an alkoxy group, a cyano group, and an amino group.

The "halogen atom" means a fluorine atom, a chlorine atom, a bromine atom, or an iodine atom, and a preferable one is a fluorine atom, a chlorine atom, or a bromine atom.

In a nucleoside derivative represented by the general formula (1), from the viewpoint that the nucleoside derivative of the present invention can exhibit the antiviral activity while the cytotoxicity of the derivative can be reduced, $R^1$ is preferably hydrogen, fluorine, chlorine, or bromine, $R^2$ is preferably hydrogen, fluorine, chlorine, or bromine, $R^3$ is preferably a cyano group, a methyl group, an ethenyl group, an ethynyl group, a monofluoromethyl group, or a hydroxymethyl group, $R^4$ is preferably an amino group, fluorine, chlorine, or a hydroxy group, $R^5$ is preferably nitrogen or a methine group, $R^6$ is preferably hydrogen or a hydroxy group, and $R^7$ is preferably hydrogen or a hydroxy group.

More specifically, examples of a nucleoside derivative having a preferable functional group include the following compounds:

a nucleoside derivative represented by the general formula (1) where $R^1$ is fluorine, chlorine, or bromine, $R^2$ is hydrogen, $R^3$ is a cyano group, an ethenyl group, an ethynyl group, or hydroxymethyl group, $R^4$ is an amino group, fluorine, chlorine, or a hydroxy group, $R^5$ is nitrogen or a methine group, $R^6$ is hydrogen, and $R^7$ is hydrogen;

a nucleoside derivative represented by the general formula (1) where $R^1$ is hydrogen, $R^2$ is fluorine, chlorine, or bromine, $R^3$ is a cyano group, an ethenyl group, an ethynyl group, or a hydroxymethyl group, $R^4$ is an amino group, fluorine, chlorine, or hydroxy group, $R^5$ is nitrogen or a methine group, $R^6$ is hydrogen, and $R^7$ is hydrogen;

a nucleoside derivative represented by the general formula (1) where $R^1$ is fluorine, $R^2$ is fluorine, $R^3$ is a cyano group, an ethenyl group, an ethynyl group, or hydroxymethyl group, $R^4$ is an amino group, fluorine, chlorine, or a hydroxy group, $R^5$ is nitrogen or a methine group, $R^6$ is hydrogen, and $R^7$ is hydrogen;

a nucleoside derivative represented by the general formula (1) where $R^1$ is hydrogen, $R^2$ is hydrogen, $R^3$ is a cyano group, a methyl group, a monofluoromethyl group, an ethenyl group, or an ethynyl group, $R^4$ is an amino group, $R^5$ is a methine group, $R^6$ is hydrogen, and $R^7$ is hydrogen;

a nucleoside derivative represented by the general formula (1) where $R^1$ is fluorine, chlorine, or bromine, $R^2$ is hydrogen, $R^3$ is a cyano group, an ethenyl group, an ethynyl group, or a hydroxymethyl group, $R^4$ is an amino group, fluorine, chlorine, or a hydroxy group, $R^5$ is nitrogen or a methine group, $R^6$ is hydrogen, and $R^7$ is a hydroxy group;

a nucleoside derivative represented by the general formula (1) where $R^1$ is hydrogen, $R^2$ is fluorine, chlorine, or bromine, $R^3$ is a cyano group, an ethenyl group, an ethynyl group, or a hydroxymethyl group, $R^4$ is an amino group, fluorine, chlorine, or a hydroxy group, $R^5$ is nitrogen or a methine group, $R^6$ is hydrogen, and $R^7$ is a hydroxy group;

a nucleoside derivative represented by the general formula (1) where $R^1$ is fluorine, chlorine, or bromine, $R^2$ is hydrogen, $R^3$ is a cyano group, an ethenyl group, an ethynyl group, or a hydroxymethyl group, $R^4$ is an amino group, fluorine, chlorine, or a hydroxy group, $R^5$ is nitrogen or a methine group, $R^6$ is a hydroxy group, and $R^7$ is hydrogen;

a nucleoside derivative represented by the general formula (1) where $R^1$ is hydrogen, $R^2$ is fluorine, chlorine, or bromine, $R^3$ is a cyano group, an ethenyl group, an ethynyl group, or a hydroxymethyl group, $R^4$ is an amino group, fluorine, chlorine, or a hydroxy group, $R^5$ is nitrogen or a methine group, $R^6$ is a hydroxy group, and $R^7$ is hydrogen;

a nucleoside derivative represented by the general formula (1) where $R^1$ is fluorine, $R^2$ is fluorine, $R^3$ is a cyano group, an ethenyl group, an ethynyl group, or a hydroxymethyl group, $R^4$ is an amino group, fluorine, chlorine, or a hydroxy group, $R^5$ is nitrogen or a methine group, $R^6$ is hydrogen, and $R^7$ is a hydroxy group; and a nucleoside derivative represented by the general formula (1) where $R^1$ is fluorine, $R^2$ is fluorine, $R^3$ is a cyano group, an ethenyl group, an ethynyl group, or a hydroxymethyl group, $R^4$ is an amino group, fluorine, chlorine, or a hydroxy group, $R^5$ is nitrogen or a methine group, $R^6$ is a hydroxy group, and $R^7$ is hydrogen.

Moreover, examples of a nucleoside derivative having a preferable functional group include:

a nucleoside derivative represented by the general formula (1) where $R^1$ and $R^2$ are fluorine and hydrogen, hydrogen and fluorine, or fluorine and fluorine, respectively, $R^3$ is a cyano group, $R^4$ is an amino group, $R^5$ is nitrogen, and $R^6$ and $R^7$ are both hydrogen;

a nucleoside derivative represented by the general formula (1) where $R^1$ and $R^2$ are chlorine and hydrogen or hydrogen and chlorine, respectively, $R^3$ is a cyano group, $R^4$ is an amino group, $R^5$ is nitrogen, and $R^6$ and $R^7$ are both hydrogen; and a nucleoside derivative represented by the general formula (1) where $R^1$ and $R^2$ are both hydrogen, $R^3$ is a cyano group, a methyl group, a monofluoromethyl group, an ethenyl group, or an ethynyl group, $R^4$ is an amino group, $R^5$ is nitrogen, and $R^6$ and $R^7$ are both hydrogen.

The nucleoside derivatives of the present invention also include pharmacologically acceptable salts, hydrates or solvates thereof. Such a pharmacologically acceptable salt is not particularly limited and may be appropriately selected depending on the structure and the like of the nucleoside derivative. Examples thereof include acid addition salts (such as hydrochloride, sulfate, hydrobromide, nitrate, hydrogensulfate, phosphate, acetate, lactate, succinate, citrate, maleate, hydroxymaleate, tartrate, fumarate, methanesulfonate, p-toluenesulfonate, camphor sulfonate, sulfamate, mandelate, propionate, glycolate, stearate, malate, ascorbate, pamoate, phenylacetate, glutamate, benzoate, salicylate, sulfanilate, 2-acetoxybenzoate, ethane disulfonate, oxalate, isethionate, formate, trifluoroacetic acid salt, ethyl succinate, lactobionate, gluconate, glucoheptonate, 2-hydroxyethanesulfonate, benzenesulfonate, lauryl sulfate, aspartate, adipate, hydriodide, nicotinate, oxalate, picrate, thiocyanate, and undecanoate), and base addition salts (sodium salt, potassium salt, zinc salt, calcium salt, bismuth salt, barium salt, magnesium salt, aluminum salt, copper salt, cobalt salt, nickel salt, cadmium salt, ammonium salt, ethylenediamine salt, and N-dibenzylethylenediamine salt). Then, the hydrate or solvate is not particularly limited, and an example thereof is one in which 0.1 to 3 molecules of water or a solvent are added per molecule of a nucleoside derivative or its salt.

The nucleoside derivatives of the present invention include: all isomers such as tautomers, geometrical isomers, optical isomers based on asymmetric carbons, and stereoisomers; and isomer mixtures. Furthermore, the nucleoside derivatives of the present invention also include compounds each of which can exhibit the desired activity even after the nucleoside derivative of the present invention undergoes in vivo metabolism such as oxidation, reduction, hydrolysis, amination, deamination, hydroxylation, phosphorylation, dehydroxylation, alkylation, dealkylation, or conjugation. The present invention also includes compounds (in the form of so-called prodrug) each of which undergoes metabolism such as oxidation, reduction, or hydrolysis in vivo to produce the nucleoside derivative of the present invention. Furthermore, the nucleoside derivative of the present invention can be formulated according to the known pharmaceutical manufacturing methods, as described later.

Methods for synthesizing the nucleoside derivative of the present invention are described in detailer in Examples described later. Thus, in reference to the description in Examples, those skilled in the art can synthesize the nucleoside derivative of the present invention by selecting a reaction material, a reaction reagent, reaction conditions (for example, a solvent, a reaction temperature, a catalyst, and a reaction time) and the like as appropriate, and by adding a modification or a reformation to these methods as needed.

For example, in order to synthesize the nucleoside derivative represented by the formula (1) of the present invention, a compound 16 is synthesized from a compound 1 through compounds 9 (reaction intermediates: compounds (E)-9 and (Z)-9) in the following way, as demonstrated in specific examples in Examples described later.

[Chem. 3]
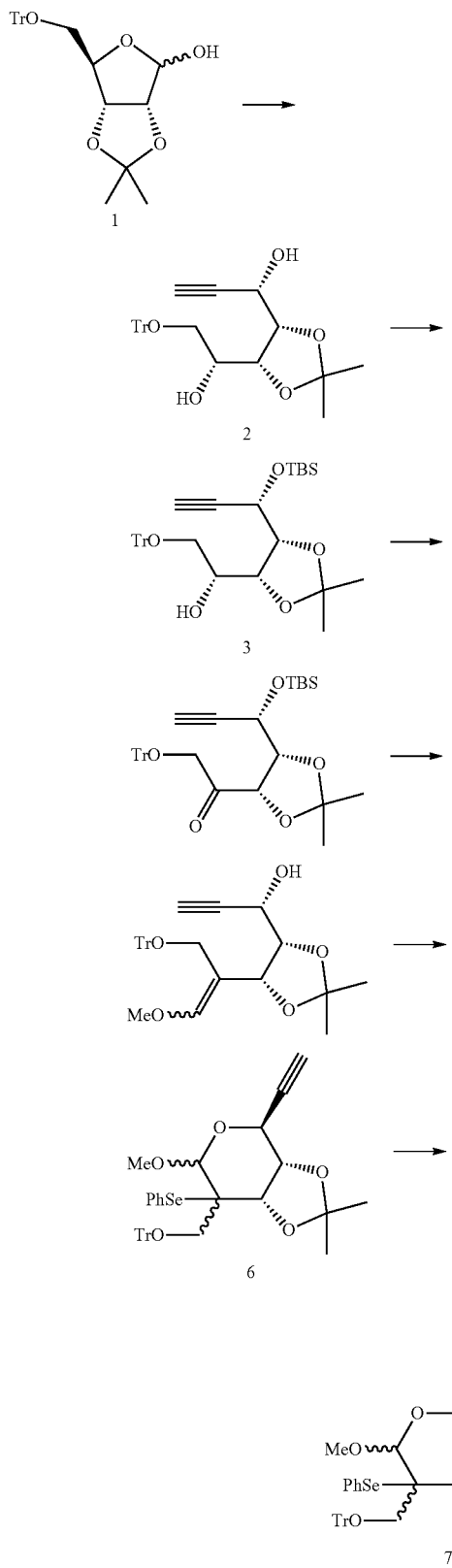
[Chem. 4]
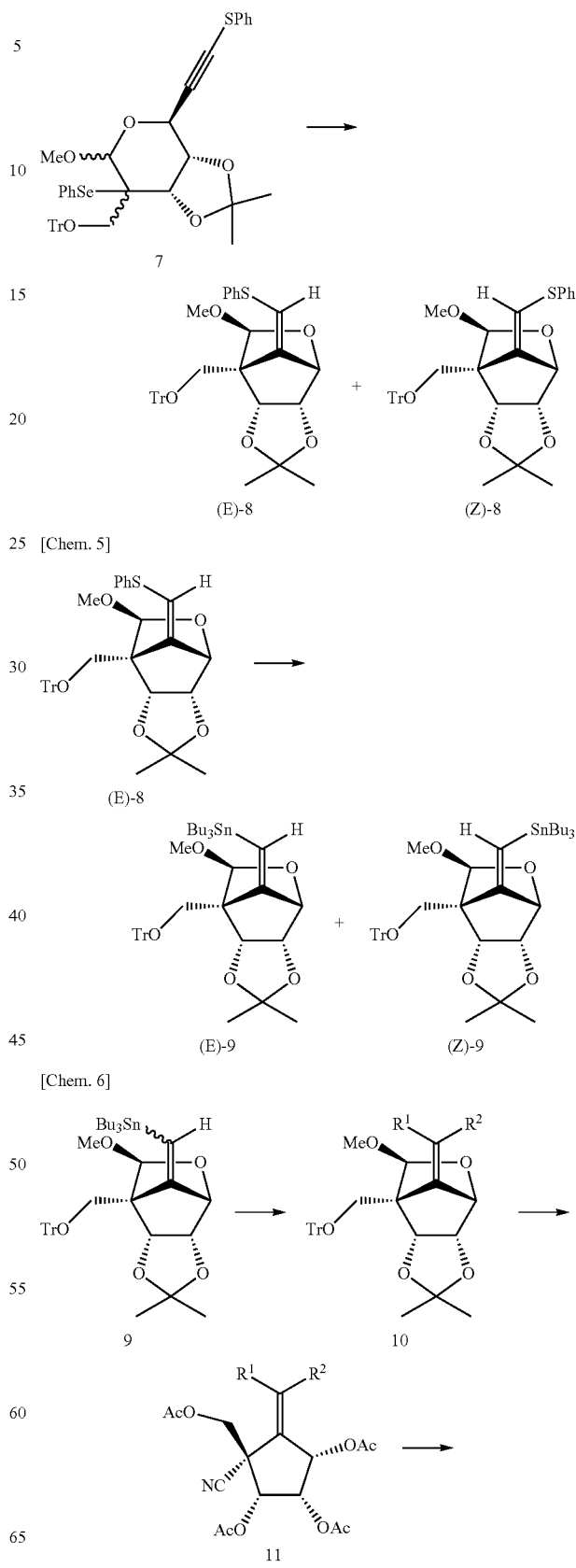
[Chem. 6]
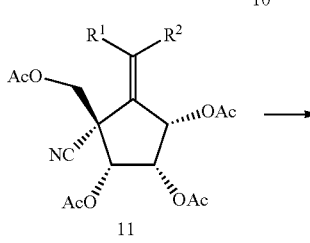

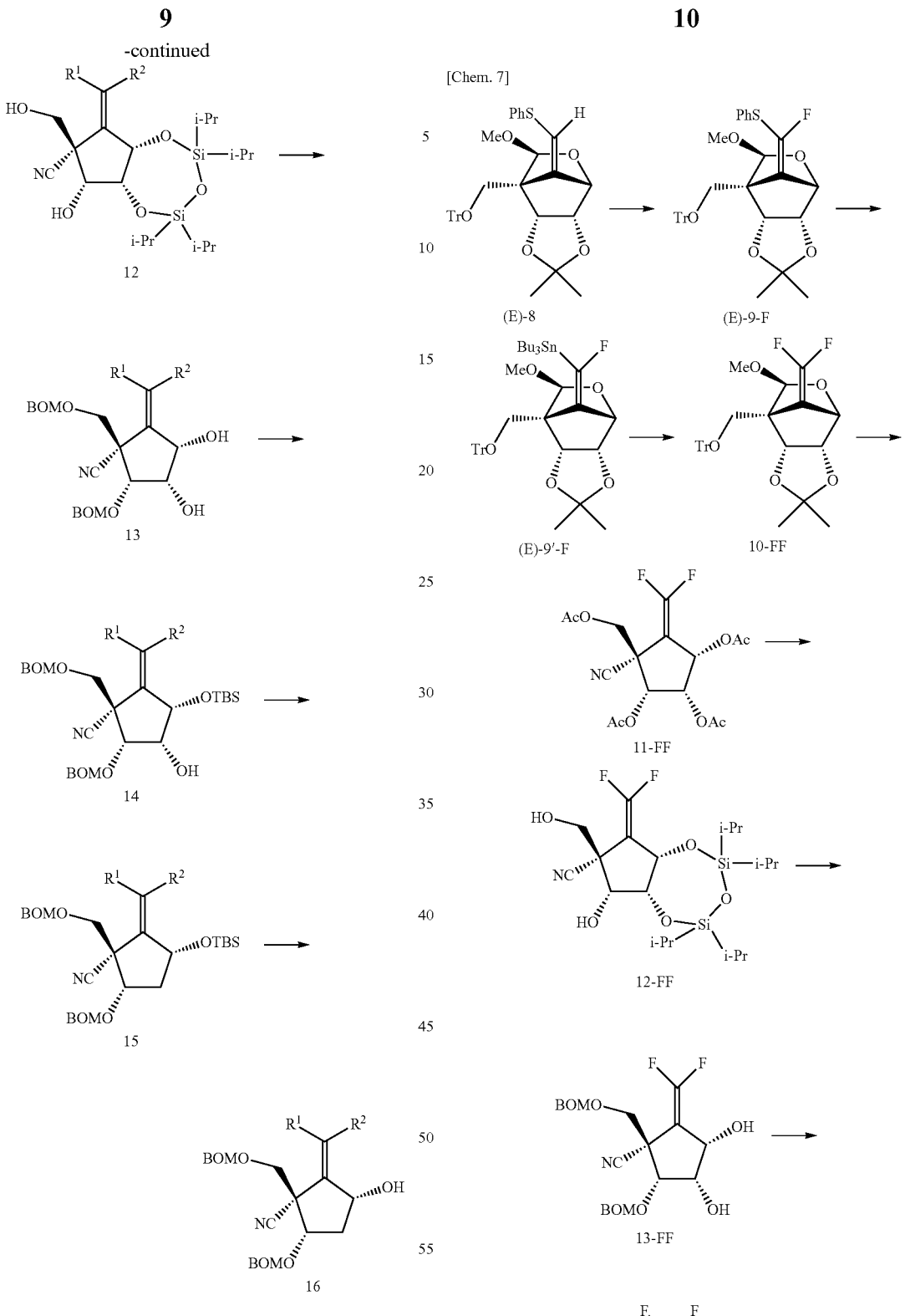

In the same way as above, in order to synthesize a nucleoside derivative represented by the following formula (1) of the present invention (where $R^1$ and $R^2$ are the same atom), for example, a compound 16 (for example, the following compound 16-FF) is firstly synthesized from the above compound (E)-8. The following reaction formula presents an example where $R^1$ and $R^2$ are both a fluorine atom.

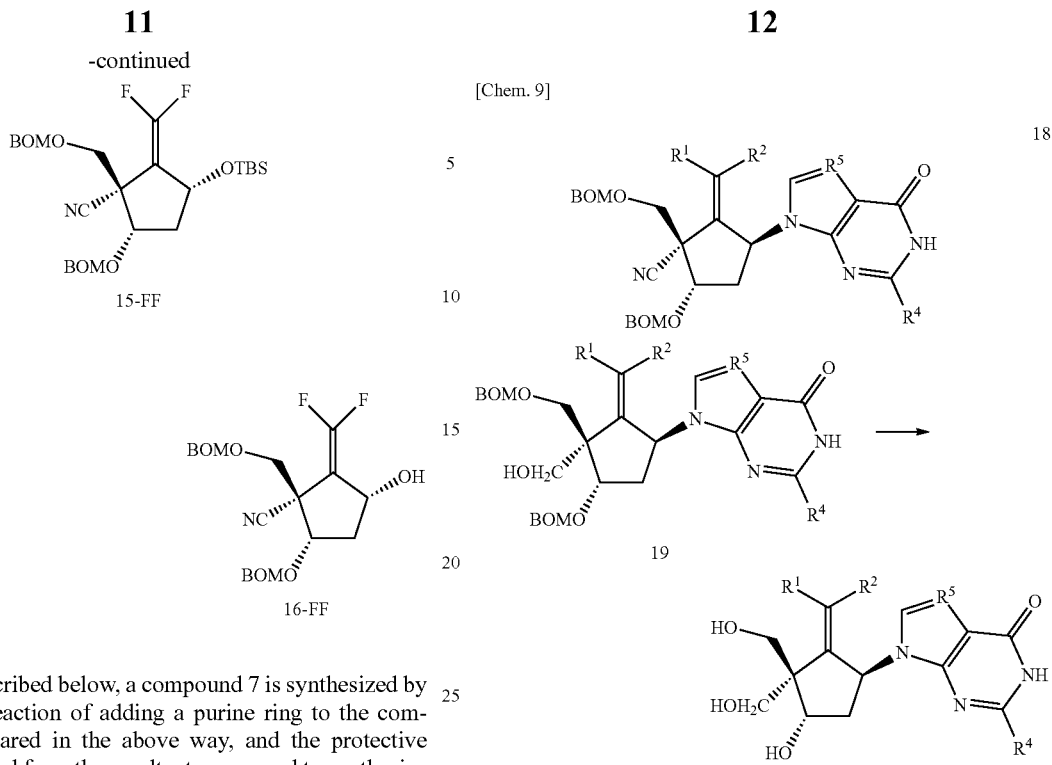

Then, as described below, a compound 7 is synthesized by a Mitsunobu reaction of adding a purine ring to the compound 16 prepared in the above way, and the protective group is removed from the resultant compound to synthesize a compound 18 (The nucleoside derivative of the present invention where $R^3$ is a cyano group).

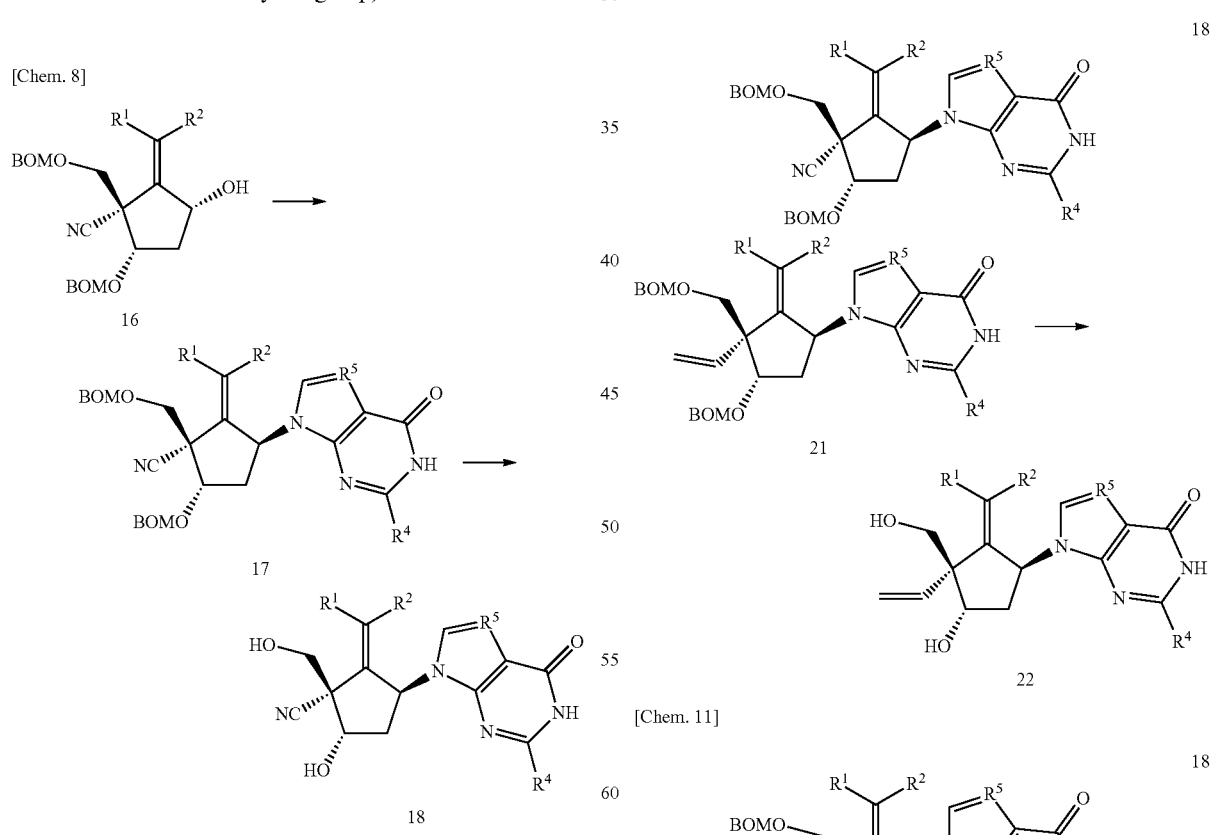

From the above-mentioned compound 18 (the nucleoside derivative of the present invention where $R^3$ is the cyano group), $R^3$ can also be replaced with another functional group as presented below, for example.

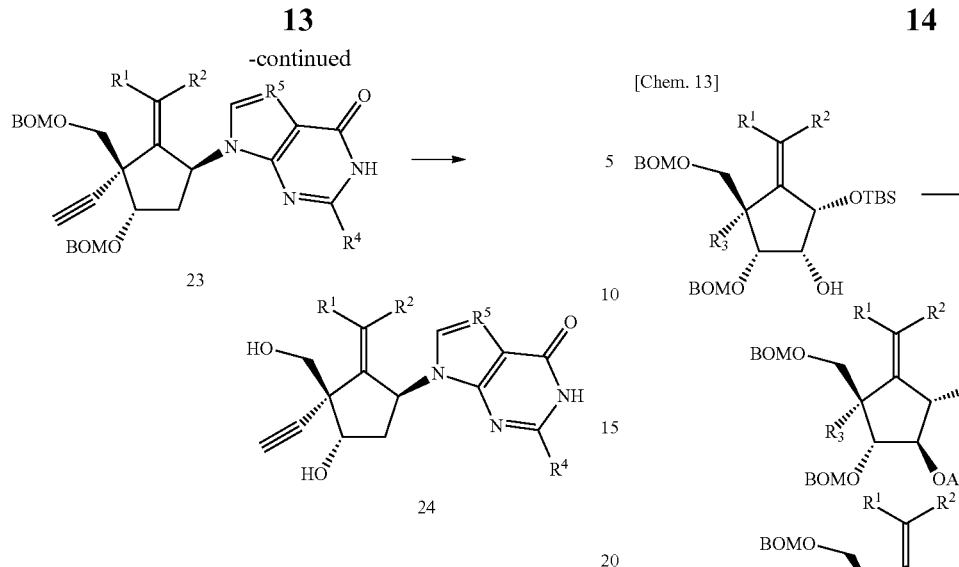

Further, the nucleoside derivative of the present invention can also be synthesized, for example, by the following reaction step.

[Chem. 12]

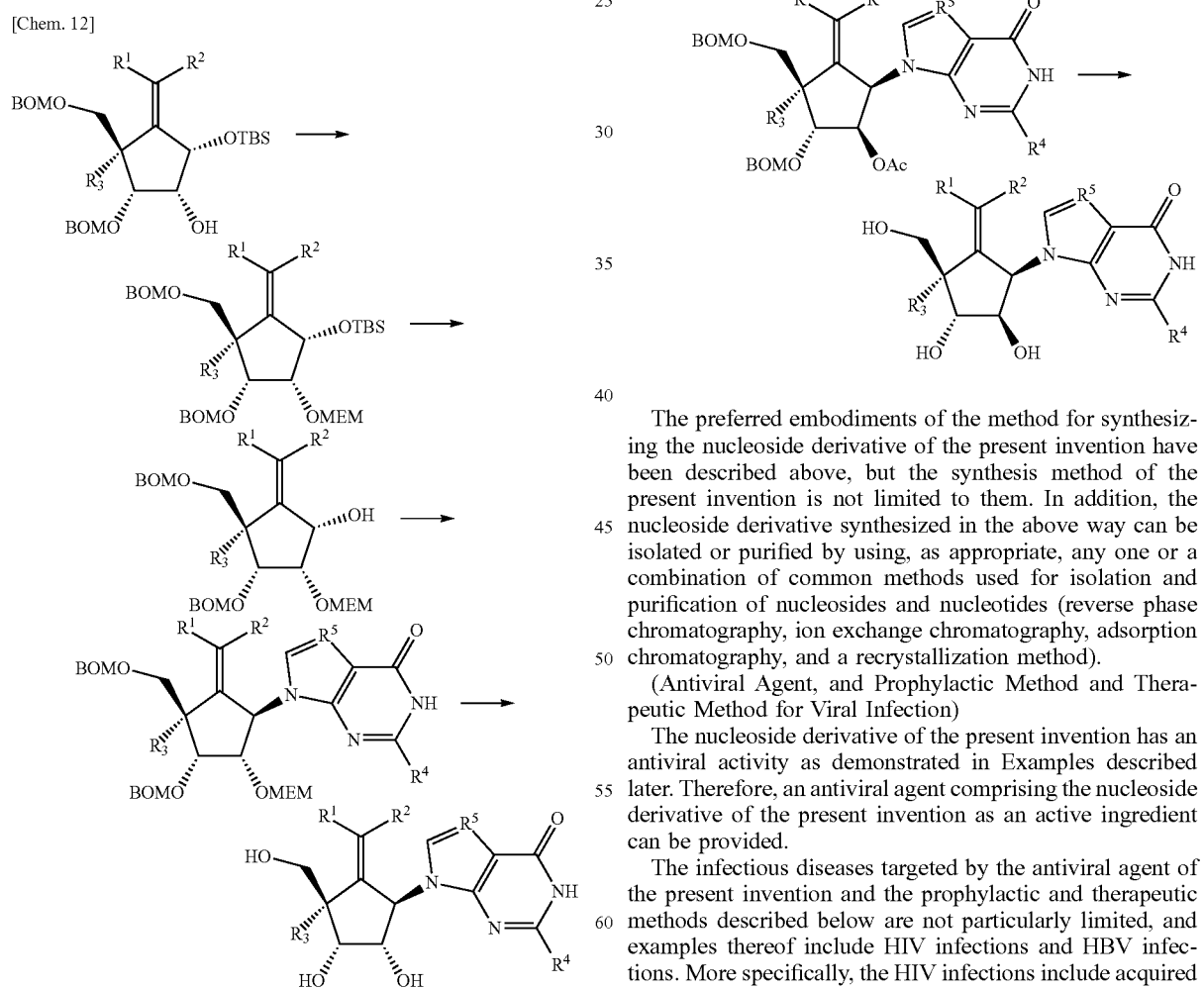

Still further, the nucleoside derivative of the present invention can also be synthesized, for example, by the following reaction step.

The preferred embodiments of the method for synthesizing the nucleoside derivative of the present invention have been described above, but the synthesis method of the present invention is not limited to them. In addition, the nucleoside derivative synthesized in the above way can be isolated or purified by using, as appropriate, any one or a combination of common methods used for isolation and purification of nucleosides and nucleotides (reverse phase chromatography, ion exchange chromatography, adsorption chromatography, and a recrystallization method).

(Antiviral Agent, and Prophylactic Method and Therapeutic Method for Viral Infection)

The nucleoside derivative of the present invention has an antiviral activity as demonstrated in Examples described later. Therefore, an antiviral agent comprising the nucleoside derivative of the present invention as an active ingredient can be provided.

The infectious diseases targeted by the antiviral agent of the present invention and the prophylactic and therapeutic methods described below are not particularly limited, and examples thereof include HIV infections and HBV infections. More specifically, the HIV infections include acquired immunodeficiency syndrome (AIDS), AIDS-related complications (ARC), persistent generalized lymphoma (PGL), AIDS-related neurological symptoms, anti-HIV antibody positive and HIV positive symptoms, Kaposi's sarcoma, thrombocytopenic purpura, and opportunistic infections, whereas the HBV infections include hepatitis B (chronic hepatitis, acute hepatitis, and fulminant hepatitis), liver cirrhosis, liver fibrosis, and hepatocellular carcinoma.

The antiviral agent of the present invention can be formulated by the known pharmaceutical manufacturing methods. For example, the antiviral agent can be used orally or parenterally in any of the forms of capsule, tablet, pill, liquid, powder, granule, fine granule, film coating, pellet, troche, sublingual tablet, masticatory, buccal, paste, syrup, suspension, elixir, emulsion, liniment, ointment, plaster, cataplasm, percutaneously absorbable preparation, lotion, aspirant, aerosol, injection, suppository, and so on.

In these preparations, the antiviral agent of the present invention can be combined as appropriate with any of pharmacologically acceptable carriers or media, specifically, such as sterile water, physiological saline, vegetable oils, solvents, bases, emulsifiers, suspending agents, surfactants, stabilizers, flavoring agents, fragrances, excipients, vehicles, antiseptic agents, binders, diluents, isotonizing agents, soothing agents, bulking agents, disintegrating agents, buffering agents, coating agents, lubricants, coloring agents, sweeteners, thickening agents, correctives, solubilizing agents, and other additives. More specifically, the carriers include solid carriers such as lactose, kaolin, sucrose, crystalline cellulose, corn starch, talc, agar, pectin, stearic acid, magnesium stearate, lecithin, and sodium chloride, and liquid carriers such as glycerin, peanut oil, polyvinyl pyrrolidone, olive oil, ethanol, benzyl alcohol, propylene glycol, and water.

In addition, the antiviral agent of the present invention may be used in combination with any of other known antiviral agents. In the cases where the target diseases are HIV infections, the known antiviral agents include, for example, reverse transcriptase inhibitors (for example, nucleoside analogs such as AZT, ddC, ddI, d4T, and 3TC (lamivudine)), HIV protease inhibitors, HIV integrase inhibitors, and HIV fusion inhibitors. In the cases where the target diseases are HBV infections, the known antiviral agents include, for example, known nucleoside analogs such as entecavir, 3TC, and adefovir, and interferons (IFN). In the case where the target diseases are HBV infections, the antiviral agent of the present invention can be used not only in antiviral therapies using the foregoing drugs, but also in combination therapies with immunotherapies (such as adrenocortical steroid hormone withdrawal therapies and oral administration of propagermanium) and hepatoprotective therapies (such as intravenous injection of a glycyrrhizin preparation and oral administration of a bile acid preparation).

A preferred administration mode of the antiviral agent of the present invention is not particularly limited but may be oral administration or parenteral administration, specific ones of which include intravenous administration, intraarterial administration, intraperitoneal administration, subcutaneous administration, intradermal administration, tracheobronchial administration, rectal administration, intramuscular administration, and administration by infusion.

The antiviral agent of the present invention can be mainly used for humans, but may also be used for non-human animals such as laboratory animals.

A dose for administering the antiviral agent of the present invention is selected as appropriate according to the age, body weight, symptom, health conditions, seriousness, and drug tolerability of a subject, an administration form, and the like. The dose of the antiviral agent of the present invention per day in terms of the amount of the nucleoside derivative as the active ingredient is usually 0.00001 to 1000 mg/kg body weight and preferably 0.0001 to 100 mg/kg body weight. The antiviral agent of the present invention in such a dose is administered to the subject in one or more divided dosages.

A product or its instruction of the antiviral agent of the present invention may be one to which a statement that the antiviral agent is for use to treat or prevent the viral infection. Here, "to attach the statement to a product or its instruction" means to attach the statement to a product itself, a container, a package, or the like, or to add the statement to a medium, which discloses the information on the product, such as a manual, a package insert, a publicity material, any other printed matter, or the like. In addition, the statement that the antiviral agent is for use to treat the viral infection may also contain, as information on an action mechanism of the antiviral agent of the present invention, information that the nucleoside derivative of the present invention, when administered, may inhibit a reverse transcriptase reaction of the virus and thereby inhibit the replication of the virus.

In this way, the present invention makes it possible to prevent or treat an infection of a subject by administering the antiviral agent of the present invention to the subject. Thus, the present invention also provides a method for preventing or treating a viral infection, the method characterized by involving administering the nucleoside derivative of the present invention.

Subjects to which the nucleoside derivative of the present invention is to be administered are not particularly limited, and examples thereof include patients infected with viruses such as HIV and HBV, virus holders before the onset of infectious diseases, and people yet to be infected with a virus.

EXAMPLES

Hereinafter, the present invention is described in more details based on Examples. It should be notes that the present invention is not limited to the following examples.

Example 1

Compounds (a compound (E)-18-F and a compound (Z)-18-F) represented by the following formula were synthesized in steps described below.

[Chem. 14]

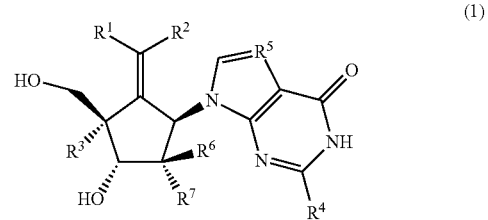

Here, the compound (E)-18-F is a compound represented by the above formula where $R^1$ is a fluorine atom, $R^2$ is a hydrogen atom, $R^3$ is a cyano group, $R^4$ is an amino group, $R^5$ is a nitrogen atom, $R^6$ is a hydrogen atom, and $R^7$ is a hydrogen atom. The compound (Z)-18-F is a compound represented by the above formula where $R^1$ is a hydrogen atom, $R^2$ is a fluorine atom, $R^3$ is a cyano group, $R^4$ is an amino group, $R^5$ is a nitrogen atom, $R^6$ is a hydrogen atom, and R[7] is a hydrogen atom. The compounds obtained in the following synthesis steps were each measured in terms of $^1$H nuclear magnetic resonance (NMR) spectrum, and ascertained to be a compound having a desired structure.

The results of these measurements are presented below as well.

(S)-1-((4S,5R)-5-((R)-1-Hydroxy-2-(trityloxy)ethyl)-2,2-dimethyl-1,3-dioxolan-4-yl)prop-2-yn-1-ol (Compound 2)

To begin with, a compound 2 was synthesized from a compound 1 in the following way.

[Chem. 15]

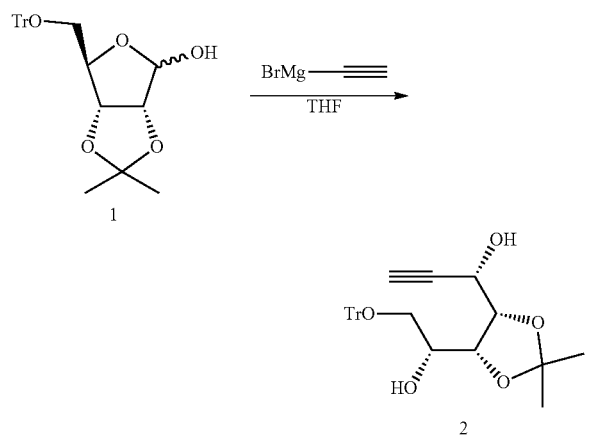

Specifically, in an argon gas flow at −80° C., ethynyl magnesium bromide (0.5 mol/L in THF, 233 mL, 116.5 mmol) was added dropwise to a THF (150 mL) solution containing the compound 1 [(see) *J. Org. Chem.*, 2004, 69, 2634.] (12.6 g, 29.13 mmol), followed by stirring for 30 minutes. The reaction mixture was returned to room temperature and further stirred for 14 hours. An aqueous solution of saturated ammonium chloride was added to the reaction mixture, and an extraction was conducted with ethyl acetate. The obtained organic layer was dried over anhydrous sodium sulfate, followed by distillation. The residue was purified by silica gel column chromatography (hexane/diethyl ether=1/2) to obtain the compound 2 (11.96 g, 90%) as a white solid.

$^1$H-NMR (CDCl$_3$, 400 MHz); δ1.33 (3H, s), 1.34 (3H, s), 3.11 (1H, d, J=3.6 Hz), 3.32 (1H, dd, J=10.0 and 7.2 Hz), 3.50 (1H, dd, J=10.0 and 2.8 Hz), 3.80-3.90 (1H, m), 4.04 (1H, d, J=4.4 Hz), 4.14 (1H, dd, J=10.0 and 5.6 Hz), 4.27 (1H, dd, J=8.4 and 5.6 Hz), 4.59-4.63 (1H, m), 7.23-7.44 (15H, m).

(R)-1-((4R,5R)-5-((S)-1-((tert-Butyldimethylsilyl)oxy)prop-2-yn-1-yl)-2,2-dimethyl-1,3-dioxolan-4-yl)-2-(trityloxy)ethan-1-ol (Compound 3)

Next, a compound 3 was synthesized as described below from the compound 2 obtained in the aforementioned step.

[Chem. 16]

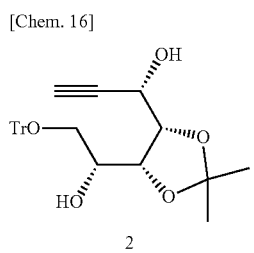

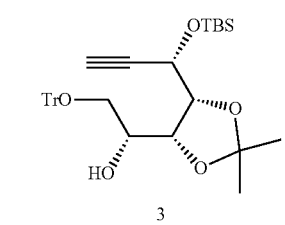

Specifically, in an argon gas flow at 0° C., TBS-Cl (4.91 g, 32.6 mmol) was added to a methylene chloride (200 mL) solution containing the compound 2 (11.96 g, 26.1 mmol) and imidazole (5.33 g, 78.24 mmol), followed by stirring for 45 minutes. The reaction mixture was brought to room temperature, and was additionally stirred for 48 hours. An aqueous solution of saturated sodium hydrogen carbonate was added to the reaction mixture, followed by extraction with methylene chloride. The obtained organic layer was dried over anhydrous sodium sulfate, followed by distillation. The residue was purified by silica gel column chromatography (hexane/diethyl ether=7/1) to obtain the compound 3 (13.54 g, 91%) as a white foam.

$^1$H-NMR (CDCl$_3$, 400 MHz); δ0.22 (3H, s), 0.24 (3H, s), 0.93 (9H, s), 1.33 (3H, s), 1.38 (3H, s), 2.49 (1H, d, J=2.4 Hz), 3.18 (1H, d, J=4.8 Hz), 3.30 (1H, dd, J=9.6 and 5.6 Hz), 3.37 (1H, dd, J=9.6 and 2.4 Hz), 3.99-4.05 (1H, m), 4.21 (1H, t, J=2.0 Hz), 4.28 (1H, dd, J=9.6 and 5.6 Hz), 4.69 (1H, dd, J=5.6 and 2.0 Hz), 7.20-7.31 (9H, m), 7.46-7.49 (6H, m).

1-((4S,5R)-5-((S)-1-((tert-Butyldimethylsilyl)oxy)prop-2-yn-1-yl)-2,2-dimethyl-1,3-dioxolan-4-yl)-2-(trityloxy)ethan-1-one (Compound 4)

Next, a compound 4 was synthesized as described below from the compound 3 obtained in the aforementioned step.

[Chem. 17]

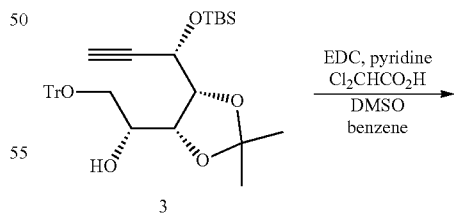

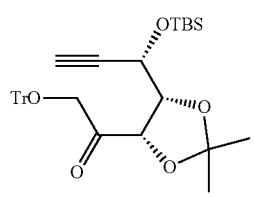

Specifically, in an argon gas flow at 0° C., dichloroacetic acid (2.17 mL, 26.3 mmol) was added dropwise to a benzene (150 mL) solution containing the compound 3 (8.36 g, 14.6 mmol), EDC hydrochloride (5.6 g, 29.2 mmol), pyridine (2.13 mL, 26.3 mmol), and DMSO (15 mL), followed by stirring for 30 minutes. The reaction mixture was returned to room temperature and further stirred for 20 hours. The reaction mixture was partitioned between an aqueous solution of saturated sodium hydrogen carbonate and ethyl acetate, and the organic layer was then dried over anhydrous sodium sulfate. After the organic layer was distilled off under reduced pressure, the residue was purified by silica gel column chromatography (hexane/diethyl ether=7/1) to obtain the compound 4 (7.5 g, 90%) as a foam.

$^1$H-NMR (CDCl$_3$, 400 MHz); δ0.04 (3H, s), 0.08 (3H, s), 0.84 (9H, s) 1.30 (3H, s) 1.44 (3H, s), 2.18 (1H, d, J=2.4 Hz), 4.29 (1H, d, J=17.2 Hz), 4.12 (1H, d, J=17.2 Hz), 4.42 (1H, dd, J=7.6 and 4.4 Hz), 4.55 (1H, dd, J=4.8 and 1.6 Hz), 4.62 (1H, d, J=7.2 Hz) 7.22-7.32 (9H, m), 7.43-7.47 (6H, m).

(S)-1-((4S,5R)-5-(1-Methoxy-3-(trityloxy)prop-1-en-2-yl)-2,2-dimethyl-1,3-dioxolan-4-yl)prop-2-yn-1-ol (Compound 5)

Next, a compound 5 was synthesized as described below from the compound 4 obtained in the aforementioned step.

[Chem. 18]

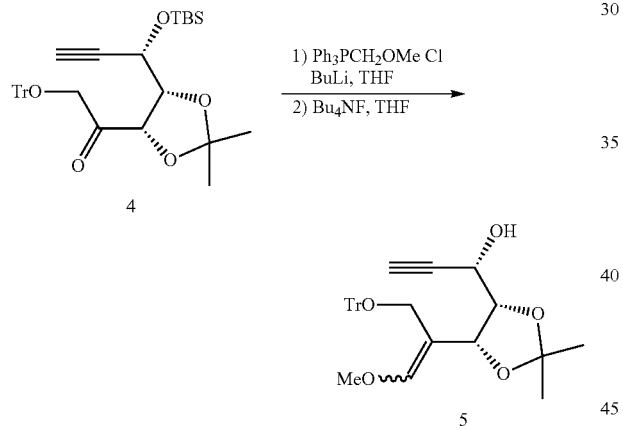

Specifically, in an argon gas flow at −80° C., butyllithium (2.66 mol/L hexane solution, 49.5 mL, 131.6 mmol) was added dropwise to an anhydrous THF (200 mL) suspension containing methoxymethyltriphenylphosphonium chloride (47.4 g, 138.4 mmol). The reaction mixture was returned to room temperature, and was further stirred for 2 hours. The reaction mixture was cooled to 0° C., and a THF (150 mL) solution containing the compound 4 (15.8 g, 27.7 mmol) was added dropwise thereto. The resultant reaction mixture was returned to room temperature and stirred for 22 hours. The reaction mixture was partitioned between an aqueous solution of saturated ammonium chloride and ethyl acetate, and the organic layer was dried over anhydrous sodium sulfate. After the organic layer was distilled off under reduced pressure, the obtained residue was dissolved in THF (100 mL). Tetrabutylammonium fluoride (1.0 mol/L THF solution, 30.5 mL, 30.5 mmol) was added to the reaction solution, and the mixture was stirred at room temperature for 5 hours. The reaction mixture was partitioned between an aqueous solution of saturated ammonium chloride and ethyl acetate, and the organic layer was dried over anhydrous sodium sulfate. After the organic layer was distilled off under reduced pressure, the obtained residue was purified by silica gel column chromatography (hexane/ethyl acetate=5/1) to obtain the compound 5 (10.34 g, 77%) as a foam.

$^1$H-NMR (CDCl$_3$, 400 MHz); δ1.31 (1.8H, s), 1.42 (1.8H, s), 1.33 (1.2H, s), 1.39 (1.2H, s), 2.30 (0.4H, 7d, J=2.0 Hz), 2.42 (0.6H, d, J=2.0 Hz), 3.20 (0.4H, d, J=5.6 Hz), 3.48 (0.6H, d, J=5.6 Hz), 3.68 (1.2H, s), 3.70-3.72 (2.4H, m), 3.94 (0.6H, d, J=10.4 Hz), 4.00-4.03 (0.6H, m), 4.17-4.25 (1.4H, m), 4.36-4.38 (0.8H, m), 4.51 (0.6H, d, J=5.6 Hz), 5.10 (0.4H, d, J=6.4 Hz), 6.21 (1.2H, s), 6.46 (1.8H, s) 7.21-7.25 (4H, m), 7.29-7.33 (5H, m), 7.45-7.49 (6H, m).

(3aS,4S,7aS)-4-Ethynyl-6-methoxy-2,2-dimethyl-7-(phenylselanyl)-7-((trityloxy)methyl)tetrahydro-4H-[1, 3]dioxolo[4,5-c]pyran (Compound 6)

Next, a compound 6 was synthesized as described below from the compound 5 obtained in the aforementioned step.

[Chem. 19]

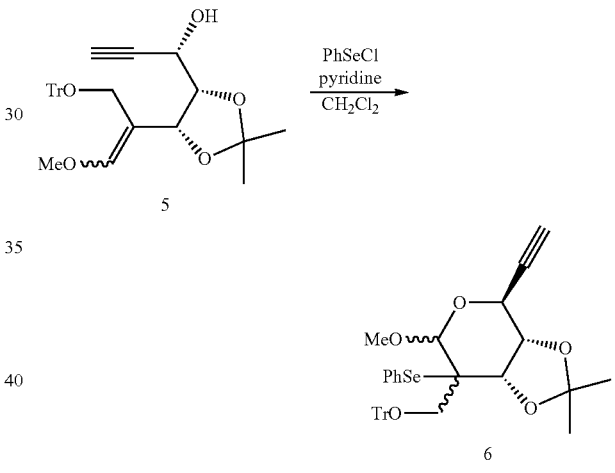

Specifically, in an argon gas flow at −80° C., phenylselenenyl chloride (6.07 g, 31.6 mmol) was added to a methylene chloride (200 mL) solution containing the compound 5 (14.6 g, 30.12 mmol) and pyridine (24.4 mL, 301.2 mmol), followed by stirring for 4.5 hours. The reaction mixture was returned to room temperature, and then further stirred for 20 hours. The reaction mixture was partitioned between an aqueous solution of saturated sodium hydrogen carbonate and methylene chloride, and the organic layer was dried over anhydrous sodium sulfate. After the organic layer was distilled off under reduced pressure, the obtained residue was purified by silica gel column chromatography (toluene) to obtain the compound 6 (16.24 g, 84%) as a foam.

$^1$H-NMR (CDCl$_3$, 500 MHz); δ1.19 (1.5H, s), 1.22 (1.5H, s), 1.48 (1.5H, s), 1.51 (1.5H, s), 2.53 (0.5H, d, J=1.8 Hz), 2.54 (0.5H, d, J=2.3 Hz), 3.32-3.36 (1H, m), 3.46 (1.5H, s), 3.50 (1.5H, s), 3.54-0.60 (1H, m), 3.80 (0.5H, d, J=7.2 Hz), 4.01 (0.5H, d, J=4.5 Hz), 4.19-4.23 (1.5H, m), 4.40 (0.5H, d, J=3.5 Hz), 4.72 (0.5H, s), 4.77 (0.5H, s), 7.15-7.33 (12H, m), 7.40-7.45 (6H, m), 7.59-7.61 (2H, m).

(3aS,4S,7aS)-6-Methoxy-2,2-dimethyl-7-(phenylselanyl)-4-((phenylthio)ethynyl)-7-((trityloxy)methyl)tetrahydro-4H-[1,3]dioxolo[4,5-c]pyran (Compound 7)

Next, a compound 7 was synthesized as described below from the compound 6 obtained in the aforementioned step.

[Chem. 20]

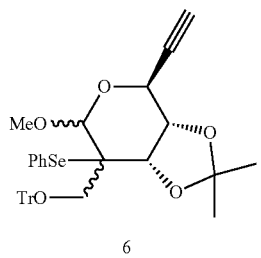

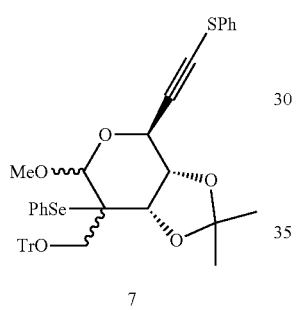

Specifically, in an argon gas flow at −80° C., LDA (1.5 mol/L THF solution, 7.83 mL, 11.75 mmol) was added dropwise to an anhydrous THF (60 mL) solution containing the compound 6 (4.05 g, 5.87 mmol), followed by stirring for 10 minutes. The reaction mixture was stirred at room temperature for 10 minutes, and thereafter was again cooled to −80° C. Then, a THF (25 mL) solution containing S-phenyl benzenesulfonothioate (2.94 g, 11.75 mmol) was added dropwise to the reaction mixture. After the reaction mixture was stirred at −80° C. for 30 minutes, LDA (3.92 mL, 5.87 mmol) was further added. The reaction mixture was partitioned between an aqueous solution of saturated ammonium chloride and ethyl acetate, and the organic layer was dried over anhydrous sodium sulfate. After the organic layer was distilled off under reduced pressure, the obtained residue was dried by silica gel column chromatography (toluene) to obtain the compound 7 (3.46 g, 79%) as a foam.

$^1$H-NMR (CDCl$_3$, 400 MHz); δ1.21 (1.8H, s), 1.23 (1.2H, s)、1.48 (1.2H, s)、1.52 (1.8H, s)、3.35 (0.4H, d、J=10.0 Hz), 3.39 (0.6H, d、J=10.4 Hz), 3.48-3.52 (3.6H, m), 3.58 (0.4H, d、J=10.0 Hz), 3.80 (0.6H, d、J=10.4 Hz), 4.07 (0.6H, d, J=4.8 Hz), 4.20 (0.4H, dd, J=8.8 and 4.8 Hz), 4.39 (0.6H, d, J=9.2 Hz), 4.40 (0.4H, d, J=8.8 Hz), 4.44 (0.4H、d、J=4.8 Hz), 4.74 (0.6H, s), 4.80 (0.4H, s), 7.16-7.20 (6H. m)、7.22-7.31 (4H, 7.33-7.36 (4H, m)、7.39-7.46 (9H, m), 7.62-7.64 (2H, m).

(3aS,4S,6S,7S,7aR,E)-6-methoxy-2,2-dimethyl-8-((phenylthio)methylene)-7-((trityloxy)methyl)tetrahydro-4H-4,7-methano[1,3]dioxolo[4,5-c]pyran and (3aS,4S,6S,7S,7aR,Z)-6-Methoxy-2,2-dimethyl-8-((phenylthio)methylene)-7-((trityloxy)methyl)tetrahydro-4H-4,7-methano[1,3]dioxolo[4,5-c]pyran (Compound (E)-8 and a compound (Z)-8)

Next, a compound (E)-8 and a compound (Z)-8 were synthesized as described below from the compound 7 obtained in the aforementioned step.

[Chem. 21]

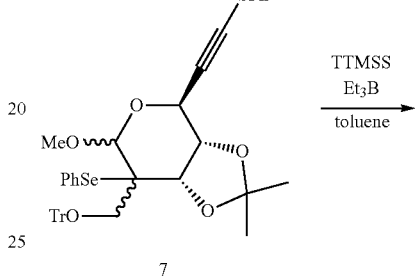

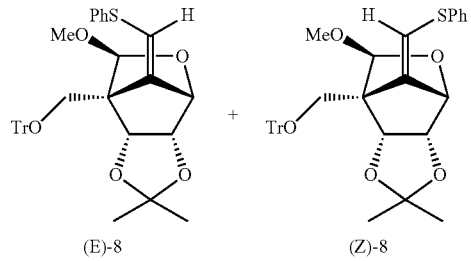

Specifically, in an oxygen gas flow at room temperature, triethylborane (1.0 mol/L THF solution, 9.25 mL, 9.25 mmol) was added to a toluene (90 mL) solution containing the compound 7 (3.46 g, 4.62 mmol) and tristrimethylsilylsilane (2.85 mL, 9.25 mmol), followed by stirring for 30 minutes. After the reaction mixture was distilled off under reduced pressure, the residue was purified by silica gel column chromatography to obtain both of the compound (Z)-8 (hexane/ethyl acetate=6/1, 277 mg, 10%, foam) and the compound (E)-8 (hexane/ethyl acetate=4/1, 2.36 g, 86%, foam).

Compound (E)-8; $^1$H-NMR (CDCl$_3$, 400 MHz); δ1.40 (3H, s)、1.673H, s)、3.42 (3H, s)、3.64 (1H, d, J=8.8 Hz)、3.81 (1H, d、J=9.6 Hz)、4.30-4.32 (2H, m)、4.57-4.59 (1H, m)、5.31 (1H, s)、6.24 (1H, s)、7.20-7.25 (7H、m)、7.28-7.38 (7H、m)、7.51-7.54 (6H, m).

Compound (Z)-8; $^1$H-NMR (CDCl$_3$, 400 MHz); δ1.41 (3H, s)、1.63 (3H, s)、3.30-3.32 (4H, m)、3.63 (1H, d, J=9.6 Hz), 4.34-4.37 (4H, m)、4.69 (1H, s)、4.76 (1H, d, J=8.0 Hz), 5.06 (1H, s), 5.86 (1H, s)、7.21-7.25 (8H, m)、7.25-7.30 (6H、m)、7.44-7.46 (6H, m).

Tributyl((E)-((3aS,4S,6S,7S,7aR)-6-methoxy-2,2-dimethyl-7-((trityloxy)methyl)tetrahydro-4H-4,7-methano [1,3]dioxolo[4,5-c]pyran-8-ylidene)methyl)stannane and Tributyl((Z)-((3aS,4S,6S,7S,7aR)-6-methoxy-2,2-dimethyl-7-((trityloxy)methyl)tetrahydro-4H-4,7-methano[1,3]dioxolo[4,5-c]pyran-8-ylidene)methyl)stannane (Compound (E)-9 and compound (Z)-9)

Next, a compound (E)-9 and a compound (Z)-9 were synthesized as described below from the compound (E)-8 obtained in the aforementioned step.

[Chem. 22]

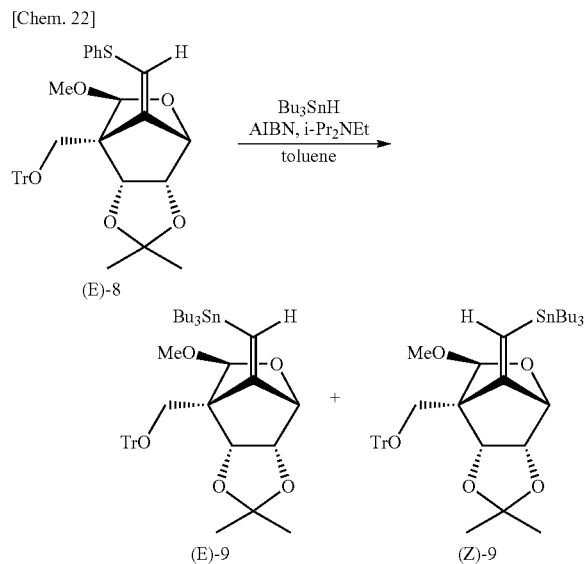

(E)-8

(E)-9    (Z)-9

In an argon gas flow, a toluene (60 mL) solution containing the compound (E)-8 (3.24 g, 5.47 mmol), ethyldiisopropylamine (3.87 mL, 21.9 mmol), tributyltin hydride (5.89 mL, 21.9 mmol) and azobisisobutyronitrile (898 mg, 5.47 mmol) was heated to reflux for 25 hours. After the organic layer was distilled off under reduced pressure, the residue was purified by silica gel column chromatography to obtain both of the compound (Z)-9 (hexane/diethyl ether=7/1, 1.17 g, 28%, oily substance) and the compound (E)-9 (hexane/diethyl ether=2/1, 2.62 g, 62%, oily substance).

Compound (E)-9; $^1$H-NMR (CDCl$_3$, 400 MHz); δ0.51-0.65 (6H, m)、0.78-0.88 (9H, m)、1.08-1.18 (6H, m), 1.28-1.33 (6H, m)、1.40 (3H, s)、1.68 (3H, s)、3.29 (1H, d, J=8.0 Hz), 3.38 (3H, s)、3.63 (1H, d, J=8.0 Hz), 4.13 (1H、d、J=2.0 Hz), 4.27 (1H, dd、J=8.0 and 2.0 Hz), 4.36 (1H, d、J=8.0 Hz), 5.33 (1H, s)、5.65-5.74 (1H, m)、7.20-7.31 (9H, m), 7.52-7.584 (6H, m).

Compound (Z)-9; $^1$H-NMR (CDCl$_3$, 400 MHz); δ0.71-0.88 (15H, m), 1.15-1.30 (6H、m)、1.33 (3H, s), 1.34-1.43 (6H、m)、1.56 (3H, s), 3.17 (1H, d, J=9.2 Hz), 3.25 (3H、s)、3.52 (1H, d, J=9.2 Hz), 4.02 (1H, br-s), 4.19 (1H, dd, J=8.4 and 2.0 Hz), 4.52 (1H, d, J=8.4 Hz), 5.07 (1H, s), 5.36-5.51 (1H, m)、7.14-7.24 (9H, m)、7.40-7.42 (6H, m).

Thereafter, the compound (E)-18-F was first synthesized through a series of steps described below from the compound (E)-9 obtained in the aforementioned step.

(3aS,4S,6S,7S,7aR,E)-8-(Fluoromethylene)-6-methoxy-2,2-dimethyl-7-((trityloxy)methyl)tetrahydro-4H-4,7-methano[1,3]dioxolo[4,5-c]pyran (Compound (E)-10-F)

To begin with, a compound (E)-10-F was synthesized as described below from the compound (E)-9 obtained in the aforementioned step.

[Chem. 23]

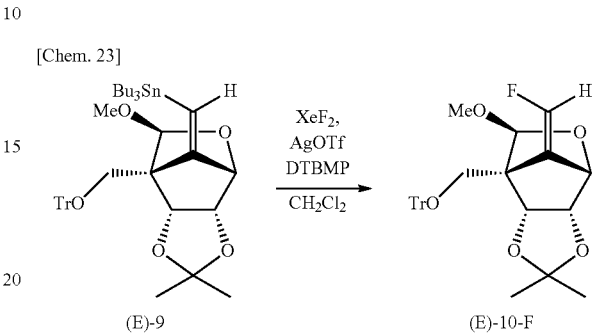

(E)-9        (E)-10-F

Specifically, in an argon gas flow at 0° C., silver trifluoromethanesulfonate (663 mg, 2.58 mmol) was added to a methylene chloride (50 mL) solution containing the compound (E)-9 (1.91 g, 2.46 mmol), 2,6-di-t-butyl-4-methylpyridine (1.11 g, 5.41 mmol) and xenon fluoride (584 mg, 3.45 mmol), followed by stirring at room temperature for 15 minutes. After the reaction mixture was partitioned between methylene chloride and an aqueous solution of saturated sodium hydrogen carbonate, the organic layer was dried over anhydrous sodium sulfate. After the organic layer was distilled off under reduced pressure, the obtained residue was purified by silica gel column chromatography (hexane/ethyl acetate=5/1) to obtain the compound (E)-10-F (968 mg, 78%) as a solid.

$^1$H-NMR (CDCl$_3$, 500 MHz); δ1.39 (3H、s)、1.66 (3H、s)、3.40 (3H、s)、3.51 (1H, d, J=10.0 Hz), 3.75 (1H, d, J=10.0 Hz), 4.29 (1H, dd, J=8.0 and 2.0 Hz), 4.39 (1H, t, J=2.0 Hz), 4.54 (1H, d, J=8.0 Hz), 5.25 (1H, s), 6.60 (1H, d, JC, F=82.2 Hz)、7.22-7.26 (3H, m), 7.28-7.35 (6H, m), 7.49-7.51 (6H, m).

(1S,2R,3R,4S,E)-4-(Acetoxymethyl)-4-cyano-5-(fluoromethylene)cyclopentane-1,2,3-triyl triacetate (Compound (E)-11-F)

Next, a compound (E)-11-F was synthesized as described below from the compound (E)-10-F obtained in the aforementioned step.

[Chem. 24]

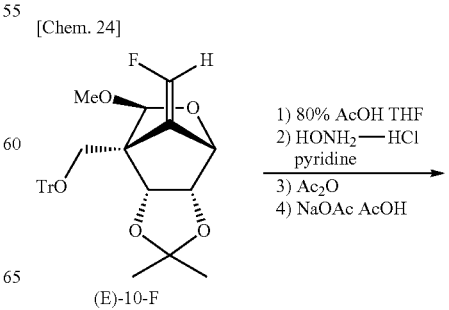

(E)-10-F 1) 80% AcOH THF
2) HONH$_2$—HCl pyridine
3) Ac$_2$O
4) NaOAc AcOH

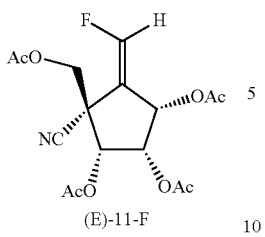

(E)-11-F

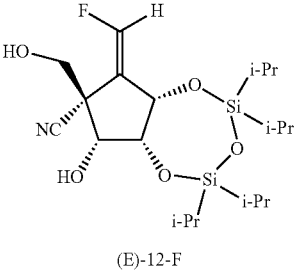

(E)-12-F

Specifically, 80% acetate (30 mL) was added to a THF (5 mL) solution containing the compound (E)-10-F (1.99 g, 3.96 mmol), followed by stirring at 80° C. for 6 hours. The reaction mixture was distilled off under reduced pressure, thereafter azeotroped three times with ethanol (20 mL), and dried under reduced pressure. Pyridine (40 mL) and hydroxylamine hydrochloride (1.28 g, 19.8 mmol) were added to the residue, followed by stirring at room temperature for 1 hour. Acetic anhydride (9.34 mL, 99 mmol) was added to the reaction mixture, followed by further stirring for 12 hours. Methanol (10 mL) was added to the reaction solution, and the mixture was stirred for 10 minutes and then distilled off under reduced pressure. The residue was partitioned between an aqueous solution of saturated sodium hydrogen carbonate and chloroform, and the organic layer was dried over anhydrous sodium sulfate and distilled off under reduced pressure. Sodium acetate (26 mg) and acetic acid (60 mL) were added to the residue, and the mixture was heated to 100° C. for 48 hours. After the reaction solution was distilled off under reduced pressure, the residue was purified by silica gel column chromatography (hexane/ethyl acetate=1/1) to obtain the compound (E)-11-F (1.33 g, 90%) as a solid.

$^1$H-NMR (CDCl$_3$, 400 MHz); δ2.12 (3H, s), 2.143H, s), 2.153H, s), 2.183H, s), 4.16 (1H, d 、 J=11.2 Hz), 4.35 (1H, d 、 J=11.2 Hz), 5.29 (1H, d, J=4.4 Hz), 5.45 (1H, d 、 J=4.4 Hz), 6.01-6.04 (1H 、 m) 7.02 (1H, dd, JC 、 F=76.8 Hz, J=2.4 Hz).

(5aS,7S,8R,8aR,E)-6-(Fluoromethylene)-8-hydroxy-7-(hydroxymethyl)-2,2,4,4-tetraisopropyltetrahydro-6H-cyclopenta[f][1,3,5,2,4]trioxadisilepine-7-carbonitrile (Compound (E)-12-F)

Next, a compound (E)-12-F was synthesized as described below from the compound (E)-11-F obtained in the aforementioned step.

[Chem. 25]

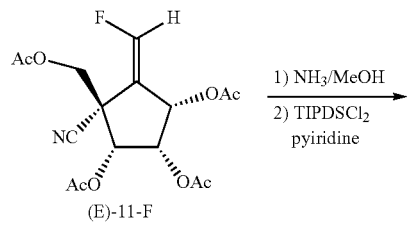

(E)-11-F

1) NH$_3$/MeOH
2) TIPDSCl$_2$
   pyiridine

Specifically, methanolic ammonia (saturated at 0° C., 35 mL) was added to the compound (E)-11-F (1.33 g, 3.58 mmol) and the mixture was stored at 4° C. for 20 hours. The reaction solution was distilled off under reduced pressure and thereafter azeotroped three times with toluene (20 mL). The residue obtained by drying the resultant solution under reduced pressure for 24 hours by a vacuum pump was mixed with pyridine (36 mL), and the mixture was cooled to −30° C. in an argon gas flow. Then, 1,3-dichloro-1,1,3,3-tetraisopropyldisiloxane (1.24 mL, 3.94 mmol) was added dropwise to the reaction solution, followed by stirring at room temperature for 16 hours. Ethanol (10 mL) was added to the reaction solution, followed by distillation under reduced pressure. Thereafter, the residue was purified by silica gel column chromatography (hexane/ethyl acetate=5/7) to obtain the compound (E)-12-F (1.11 g, 69%) as a solid.

$^1$H-NMR (CDCl$_3$, D$_2$O 、 400 MHz); δ0.90-1.09 (28H, m) 、 3.97 (1H, d, J=11.2 Hz), 4.02 (1H, d, J=11.2 Hz), 4.27 (1H, d, J=3. 2 Hz), 4.42 (1H, dd, J=6.0 and 3.2 Hz), 4.68-4.69 (1H, m), 6.70 (1H, dd, JC, F=80.8 Hz, J=2.8 Hz).

(1S,2R,3S,4S,E)-2-((Benzyloxy)methoxy)-1-(((benzyloxy)methoxy)methyl)-5-(fluoromethylene)-3,4-dihydroxycyclopentane-1-carbonitrile (Compound (E)-13-F)

Next, a compound (E)-13-F was synthesized as described below from the compound (E)-12-F obtained in the aforementioned step.

[Chem. 26]

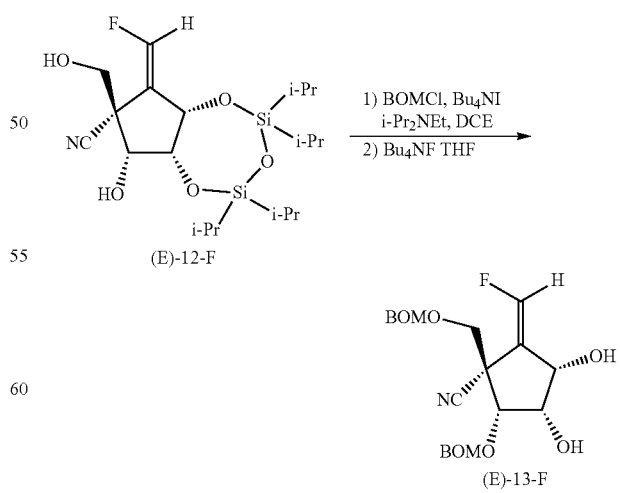

Specifically, in an argon gas flow, a 1,2-dichloroethane (25 mL) solution containing the compound (E)-12-F (1.11 g, 2.49 mmol) benzyl chloromethyl ether (2.07 mL, 14.9 mmol), ethyldiisopropylamine (4.34 mL, 24.9 mmol) and tetrabutylammonium iodide (1.84 g, 4.98 mmol) was heated and stirred at 50° C. for 72 hours. Methanol (5 mL) was added to the reaction solution, and the mixture was stirred at room temperature for 30 minutes and then partitioned between chloroform and an aqueous solution of saturated sodium hydrogen carbonate. The organic layer was dried over anhydrous sodium sulfate and then distilled off under reduced pressure. A THF (25 mL) solution containing the residue was cooled to 0° C., and tetrabutylammonium fluoride (1.0 mol/L THF solution, 4.98 mL, 4.98 mmol) was added thereto, followed by stirring for 2 hours. After the reaction mixture was distilled off under reduced pressure, the residue was purified by silica gel column chromatography (hexane/ethyl acetate=1/3) to obtain the compound (E)-13-F (748 mg, 68%) as an oily substance.

$^1$H-NMR (CDCl$_3$, 400 MHz); δ2.51 (1H, d, J=10.8 Hz), 2.96 (1H, d, J=3.2 Hz), 3.82 (1H, d, J=9.6 Hz), 3.92 (1H, d, J=9.6 Hz), 4.08-4.09 (1H, m), 4.24 (1H, d, J=3.6 Hz), 4.39-4.01 (1H, m), 4.57 (2H, s), 4.73-4.76 (4H, m), 4.96 (1H, s), 6.89 (1H, dd, JC, F=79.6 Hz、J=2.0 Hz)、7.28-7.37 (10H, m).

(1S,2R,3R,4S,E)-2-((Benzyloxy)methoxy)-1-(((benzyloxy)methoxy)methyl)-4-((tert-butyldimethylsilyl)oxy)-5-(fluoromethylene)-3-hydroxycyclopentane-1-carbonitrile (Compound (E)-14-F)

Next, a compound (E)-14-F was synthesized as described below from the compound (E)-13-F obtained in the aforementioned step.

[Chem. 27]

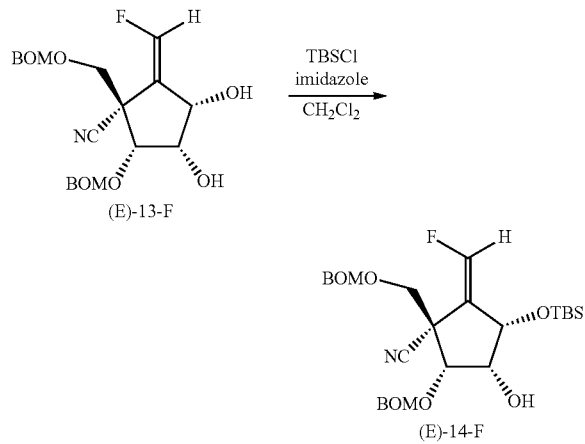

(E)-13-F (E)-14-F

Specifically, in an argon gas flow at 0° C., t-butylchlorodimethylsilane (167 mg, 1.1 mmol) was added to a methylene chloride (5 mL) solution containing the compound (E)-13-F (204 mg, 0.46 mmol) and imidazole (94 mg, 1.38 mmol), and the mixture was returned to room temperature and stirred for 45 hours. After methanol (1 mL) was added to the reaction solution, the mixture was partitioned between methylene chloride and an aqueous solution of saturated sodium hydrogen carbonate, and the organic layer was dried over anhydrous sodium sulfate. After distillation under reduced pressure, the residue was purified by silica gel column chromatography (hexane/ethyl acetate=3/1) to obtain the compound (E)-14-F (205 mg, 80%) as an oily substance.

$^1$H-NMR (CDCl$_3$, 400 MHz); δ0.12 (3H, s), 0.13 (3H, s), 0.93 (9H, s)、2.66 (1H, d, J=2.4 Hz), 3.93 (2H, s)、4.04-4.05 (1H, m), 4.20 (1H, d, J=3.6 HZ), 4.45-4.47 (1H, m)、4.56 (2H, s), 4.71-4.79 (4H, m), 4.96 (2H, s), 6.68 (1H, dd、JC, F=79.6 Hz, J=2.4 Hz), 7.30-7.36 (10H, m).

(1S,3R,5S,E)-5-((Benzyloxy)methoxy)-1-(((benzyloxy)methoxy)methyl)-3-((tert-butyldimethylsilyl)oxy)-2-(fluoromethylene)cyclopentane-1-carbonitrile (Compound (E)-15-F)

Next, a compound (E)-15-F was synthesized as described below from the compound (E)-14-F obtained in the aforementioned step.

[Chem. 28]

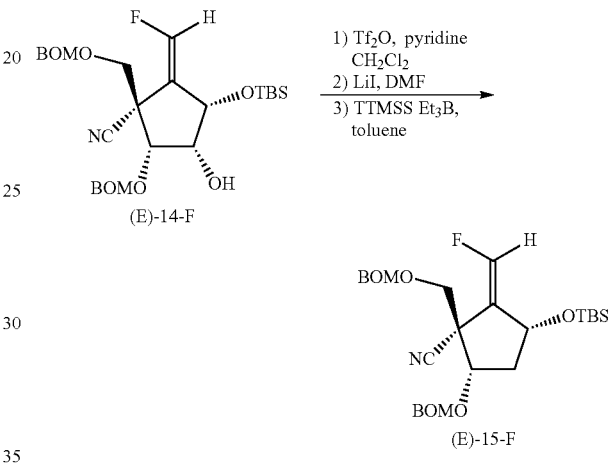

(E)-14-F (E)-15-F

Specifically, in an argon gas flow at −40° C., trifluoromethanesulfonic anhydride (140 μL, 0.82 mmol) was added dropwise to a methylene chloride (8 mL) solution containing the compound (E)-14-F (229 mg, 0.41 mmol) and pyridine (100 μL, 1.23 mmol), and the mixture was returned to room temperature and stirred for 2 hours. The reaction solution was partitioned between methylene chloride and an aqueous solution of saturated sodium hydrogen carbonate, and the organic layer was dried over anhydrous sodium sulfate and distilled off under reduced pressure. DMF (6 mL) and lithium iodide (562 mg, 4.2 mmol) were added to the residue, and the mixture was stirred under a light-shielded condition at room temperature for 22 hours. The reaction mixture was partitioned between an aqueous solution of saturated sodium hydrogen carbonate and ethyl acetate, and the organic layer was dried over anhydrous sodium sulfate and distilled off under reduced pressure. Tris(trimethylsilyl)silane (130 μL, 0.84 mmol) and triethylborane (1.0 mol/L THF solution, 420 μL, 0.42 mmol) were added to a toluene (8 mL) solution containing the residue, followed by stirring at room temperature for 20 minutes. The reaction solution was purified by silica gel column chromatography (hexane/ethyl acetate=6/1) to obtain the compound (E)-15-F (151 mg, 70%) as an oily substance.

$^1$H-NMR (CDCl$_3$, 400 MHz); δ0.07 (6H, s), 0.90 (9H, s), 1.89-1.97 (1H、m)、2.33-2.35 (1H, m), 3.85 (1H, d. J=9.6 Hz), 3.931H, d. J=9.6 Hz), 4.19 (1H, dd, J=10.4 and 6.0 Hz), 4.42-4.45 (1H, m), 4.57 (2H, s), 4.66 (1H, d. J=12.0 Hz), 4.70 (1H, d. J=12.0 Hz), 4.75 (2H, s), 4.86 (1H, d, J=6.8 Hz)、4.91 (1H, d, J=6.8 Hz) 6.71 (1H dd JC, F=80.8 Hz、J=2.4 Hz), 7.29-7.35 (10H, m).

(1S,3R,5S,E)-5-((Benzyloxy)methoxy)-1-(((benzy-loxy)methoxy)methyl)-2-(fluoromethylene)-3-hydroxycyclopentane-1-carbonitrile (Compound (E)-16-F)

Next, a compound (E)-16-F was synthesized as described below from the compound (E)-15-F obtained in the aforementioned step.

[Chem. 29]

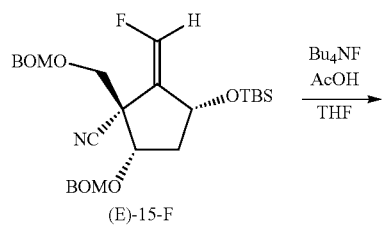

(E)-15-F

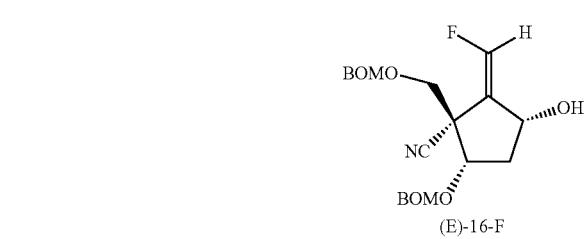

(E)-16-F

Specifically, tetrabutylammonium fluoride (1.0 mol/L THF solution, 540 μL, 0.54 mmol) was added to a THF (6 mL) solution containing the compound (E)-15-F (147 mg, 0.27 mmol) and acetate (16 μL, 0.27 mmol), followed by stirring at room temperature for 14 hours. After the reaction mixture was distilled off under reduced pressure, the residue was purified by silica gel column chromatography (hexane/ethyl acetate=1/2) to obtain the compound (E)-16-F (102 mg, 88%) as an oily substance.

$^1$H-NMR (CDCl$_3$, 400 MHz); δ1.98-2.17 (2H, m), 2.72 (1H, d, J=11.2 Hz), 3.37 (1H, d, J=10.0 Hz), 3.94 (1H, d, J=10.0 Hz), 4.53-4.55 (1H, m), 4.57 (1H, d, J=11.6 Hz), 4.651H, d, J=11.6 Hz), 4.691H, d, J=11.6 Hz), 4.751H, d, J=11.6 Hz), 4.78 (1H, d, J=6.0 Hz), 4.82 (1H, d, J=6.0 Hz), 4.91 (1H, d, J=7.2 Hz), 4.85 (1H, d, J=7.2 Hz), 7.04 (1H, d, JC, F=80.0 Hz), 7.34-7.40 (10H, m).

(1S,3S,5S,E)-3-(2-Amino-6-oxo-1,6-dihydro-9H-purin-9-yl)-2-(fluoromethylene)-5-hydroxy-1-(hydroxymethyl)cyclopentane-1-carbonitrile (Compound (E)-18-F)

Subsequently, as described below, a purine ring was added by a Mitsunobu reaction to the compound (E)-16-F obtained in the aforementioned step to synthesize a compound (E)-17-F, and then the protective group was removed from the obtained compound to obtain the compound (E)-18-F.

[Chem. 30]

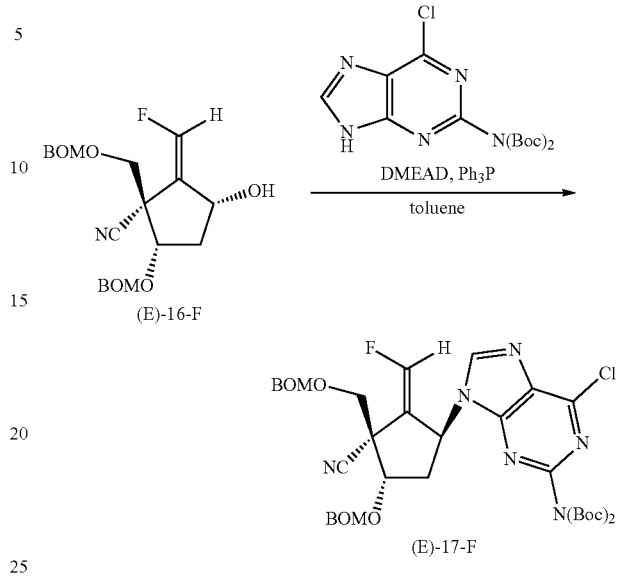

Specifically, first, in an argon gas flow at −30° C., a toluene (3 mL) solution containing azodicarboxylic acid bis-(methoxyethyl) (112 mg, 0.48 mmol) was added dropwise to a toluene (3 mL) solution containing the compound (E)-16-F (103 mg, 0.24 mmol), triphenylphosphine (126 mg, 0.48 mmol), and N2,N2-bis(t-butoxycarbonyl)-2-amino-6-chloropurine [(see) *J. Org. Chem.*, 2000, 65, 7697.] (178 mg, 0.48 mmol), and the mixture was stirred for 1 hour. The reaction mixture was returned to room temperature and then further stirred for 6 hours. The reaction solution was partitioned between saturated saline and ethyl acetate, and the organic layer was dried over anhydrous sodium sulfate and then distilled off under reduced pressure. The residue was roughly purified by silica gel column chromatography (hexane/ethyl acetate=7/5) to obtain a mixture of the compound (E)-17-F and its regioisomer. The mixture was purified by HPLC (hexane/ethyl acetate=1/1, 20 mL/min, a retention time of 8.02 minutes) to obtain the compound (E)-17-F (84 mg, 45%) as a foam.

$^1$H-NMR (CDCl$_3$, 400 MHz); δ1.47 (18H, s), 2.42-2.48 (1H, m), 2.55-2.61 (1H, m), 4.07 (1H, d, J=12.0 Hz), 4.10 (1H, d, J=12.0 Hz), 4.55-4.59 (3H, m) 、 4.67 (1H, d, J=11.6 Hz), 4.77 (1H, d, J=11.6 Hz), 4.83 (2H, s), 4.88 (1H, d, J=7.2 Hz), 4.93 (1H, d, J=7.2 Hz), 5.73-5.77 (1H, m) 、 6.67 (1H, dd, JC, F=77.2 Hz, J=2.0 Hz) 、 7.26-7.36 (10H, m), 8.20 (1H, s).

[Chem. 31]

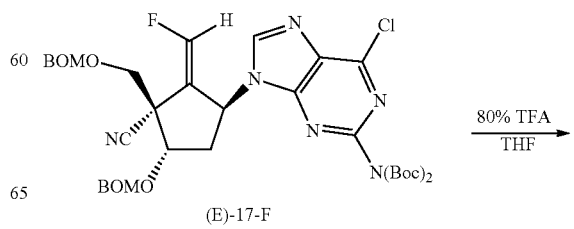

(E)-17-F

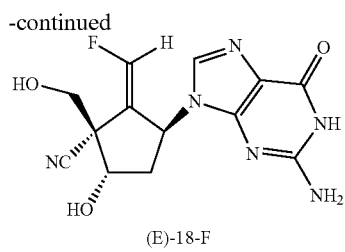

Next, 80% trifluoroacetate (4 mL) was added to a THF (1 mL) solution containing the compound (E)-17-F (84 mg, 0.11 mmol), followed by stirring at room temperature for 72 hours. The reaction solution was distilled off under reduced pressure and thereafter azeotroped three times with ethanol (5 mL). Methanolic ammonia (saturated at 0° C., 5 mL) was added to the residue, and the mixture was stored at 4° C. for 14 hours. After the reaction solution was distilled off under reduced pressure, the residue was purified by reverse phase HPLC (30% methanol, 10 mL/min, a retention time of 8.72 minutes) to obtain the compound (E)-18-F (28 mg, 81%) as a solid.

$^1$H NMR (DMSO-d6, 500 MHz) δ2.11-2.13 (1H, n), 2.48-2.50 (1H, m) 、3.78 (1H 、dd 、J=11.5 and 6.3 Hz), 3.82 (1H, dd, J=11.5 and 5.8 Hz), 4.43 (1H, br-s) 、5.52-5.56 (1H, m), 5.87 (1H, t 、J=6.3 Hz), 6.08 (1H, d 、J=4.6 Hz), 6.44 (2H, br-s) 、6.75 (1H, dd 、JC, F=79.0 Hz, 2.3 Nz) 、7.80 (1H, s) 、10.40 (1H, br-s).

In addition, the compound (Z)-18-F was also synthesized through a series of steps described below from the compound (Z)-9 obtained as above.

(3aS,4S,6S,7S,7aR,Z)-8-(Fluoromethylene)-6-methoxy-2,2-dimethyl-7-((trityloxy)methyl)tetra-hydro-4H-4,7-methano[1,3]dioxolo[4,5-c]pyran (Compound (Z)-10-F)

To begin with, a compound (Z)-10-F was synthesized as described below from the compound (Z)-9 obtained as above.

[Chem. 32]

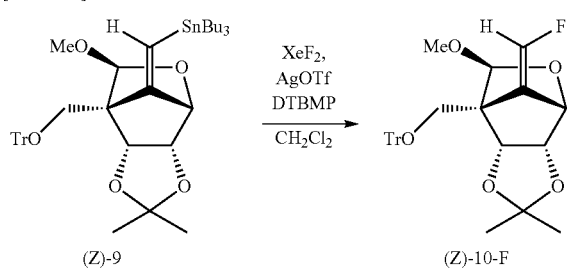

Specifically, in an argon gas flow at 0° C., silver trifluoromethanesulfonate (1.3 g, 5.06 mmol) was added to a methylene chloride (96 mL) solution containing the compound (Z)-9 (3.73 g, 4.82 mmol), 2,6-di-t-butyl-4-methylpyridine (2.47 g, 12.05 mmol), and xenon fluoride (1.14 g, 6.75 mmol), followed by stirring at room temperature for 15 minutes. After the reaction mixture was partitioned between methylene chloride and an aqueous solution of saturated sodium hydrogen carbonate, the organic layer was dried over anhydrous sodium sulfate. After the organic layer was distilled off under reduced pressure, the obtained residue was purified by silica gel column chromatography (hexane/ethyl acetate=5/1) to obtain the compound (Z)-10-F (1.01 g, 42%) as a foam.

$^1$H-NMR (CDCl$_3$, 500 MHz); δ1.40 (3H, s), 1.61 (3H, s), 3.24 (1H, d, J=9.6 Hz), 3.32 (1H, s) 、3.58 (1H, d, J=9.6 Hz), 4.38 (1H, dd, J=8.0 and 2.0 Hz), 4.76 (1H, d, J=8.0 Hz), 4.82 (1H, d, J=2.0 Hz), 5.03 (1H, d, J=3.6 Hz), 6.17 (1H, d, JC, F=83.2 Hz), 7.23-7.27 (3H, m), 7.29-7.33 (6H, m), 7.43-7.46 (6H, m).

(1S,2R,3R,4S,Z)-4-(Acetoxymethyl)-4-cyano-5-(fluoromethylene)cyclopentane-1,2,3-triyl triacetate (Compound (Z)-11-F)

Next, a compound (Z)-11-F was synthesized as described below from the compound (Z)-10-F obtained in the aforementioned step.

[Chem. 33]

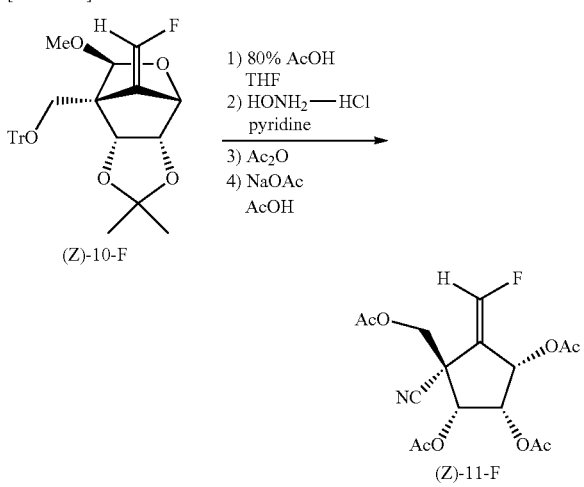

Specifically, 80% acetate (30 mL) was added to a THF (3 mL) solution containing the compound (Z)-10-F (1.17 g, 2.33 mmol), followed by stirring at 80° C. for 15 hours. The reaction mixture was distilled off under reduced pressure, thereafter azeotroped three times with ethanol (20 mL), and dried under reduced pressure. Pyridine (30 mL) and hydroxylamine hydrochloride (751 mg, 11.65 mmol) were added to the residue, followed by stirring at room temperature for 2 hours. Acetic anhydride (5.5 mL, 58.3 mmol) was added to the reaction mixture, followed by additional stirring for 12 hours. Methanol (10 mL) was added to the reaction solution, and the mixture was stirred for 10 minutes and then was distilled off under reduced pressure. The residue was partitioned between an aqueous solution of saturated sodium hydrogen carbonate and chloroform, and the organic layer was dried over anhydrous sodium sulfate and then distilled off under reduced pressure. Sodium acetate (15 mg) and acetate (30 mL) were added to the residue, and the mixture was heated to 100° C. for 48 hours. After the reaction solution was distilled off under reduced pressure, the residue was purified by silica gel column chromatography (hexane/ethyl acetate=3/2) to obtain the compound (Z)-11-F (588 mg, 68%) as a solid.

$^1$H-NMR (CDCl$_3$, 400 MHz); δ2.11 (3H, s), 2.14 (3H, s), 2.15 (3H, s), 2.18 (3H, s), 4.16 (1H, d 、J=11.6 Hz), 4.35

(1H, d 、J=11.6 Hz), 5.29 (1H, d, J=4.4 Hz) 、5.45 (1H, t, J=4.4 Hz), 6.01-6.04 (1H, m), 7.02 (1H, dd 、JC, F=76.8 Hz, J=2.0 Hz).

(5aS,7S,8R,8aR,Z)-6-(Fluoromethylene)-8-hydroxy-7-(hydroxymethyl)-2,2,4,4-tetraisopropyltetrahydro-6H-cyclopenta[f][1,3,5,2,4]trioxadisilepine-7-carbonitrile (Compound (Z)-12-F)

Next, a compound (Z)-12-F was synthesized as described below from the compound (Z)-11-F obtained in the aforementioned step.

[Chem. 34]

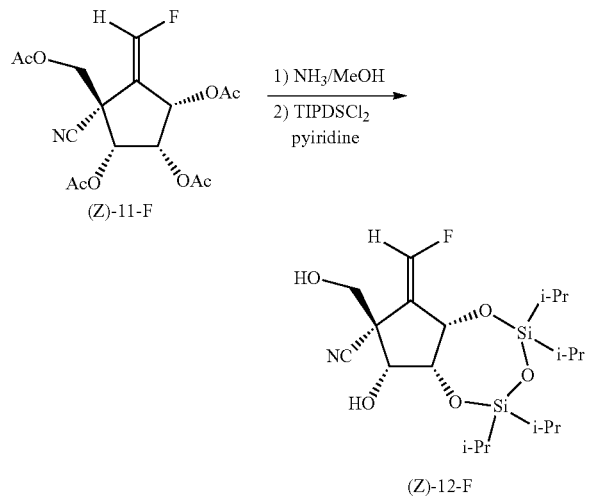

(Z)-11-F

Specifically, methanolic ammonia (saturated at 0° C., 30 mL) was added to the compound (Z)-11-F (587 mg, 1.58 mmol), and the mixture was stored at 4° C. for 24 hours. The reaction solution was distilled off under reduced pressure and thereafter azeotroped three times with toluene (20 mL). The residue obtained by drying the resultant solution for 24 hours under reduced pressure by the vacuum pump was mixed with pyridine (30 mL), and the mixture was cooled to −30° C. in an argon gas flow. Then, 1,3-dichloro-1,1,3,3-tetraisopropyldisiloxane (548 µL, 1.74 mmol) was added dropwise to the reaction solution, followed by stirring for 12 hours. The reaction solution was returned to room temperature, and then further stirred for 12 hours. The reaction solution was mixed with ethanol (10 mL) and then was distilled off under reduced pressure. Thereafter, the residue was purified by silica gel column chromatography (hexane/ethyl acetate=5/7) to obtain the compound (Z)-12-F (601 mg, 85%) as a foam.

$^1$H-NMR (CDCl$_3$, D$_2$O 、400 MHz); δ1.03-1.12 (28H, m), 2.39 (1H, dd 、J=7.2 and 5.6 Hz), 3.22 (1H, d, J=10.8 Hz), 3.73 (1H, dd, J=10.8 and 7.2 Hz), 3.87 (1H, dd, J=10.8 and 5.6 Hz) 、4.02 (1H, dd 、J=10.8 and 4.4 Hz), 4.33 (1H 、t 、J=4.0 Hz) 、5.01 (1H, br-s), 7.03 (1H, dd, JC, F=78.4 Hz, J=2.0 Hz).

(1S,2R,3S,4S,Z)-2-((Benzyloxy)methoxy)-1-(((benzyloxy)methoxy)methyl)-5-(fluoromethylene)-3,4-dihydroxycyclopentane-1-carbonitrile (Compound (Z)-13-F)

Next, a compound (Z)-13-F was synthesized as described below from the compound (Z)-12-F obtained in the aforementioned step.

[Chem. 35]

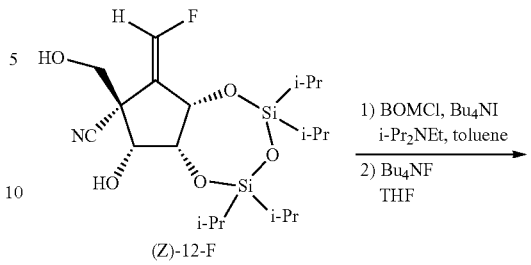

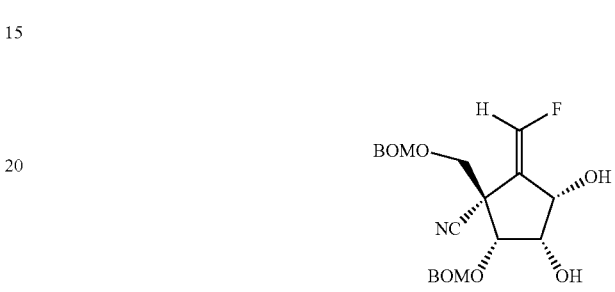

(Z)-13-F

Specifically, in an argon gas flow, a toluene (26 mL) solution containing the compound (Z)-12-F (594 mg, 1.33 mmol), benzyl chloromethyl ether (1.48 mL, 10.7 mmol), ethyldiisopropylamine (2.79 mL, 16.0 mmol), and tetrabutylammonium iodide (2.95 g, 7.98 mmol) was heated and stirred at 80° C. for 48 hours. After methanol (5 mL) was added to the reaction solution, the mixture was stirred at room temperature for 30 minutes and thereafter partitioned between ethyl acetate and an aqueous solution of saturated sodium hydrogen carbonate. The organic layer was dried over anhydrous sodium sulfate, and then distilled off under reduced pressure. After the residue was roughly purified by silica gel column chromatography (hexane/ethyl acetate=4/1), a THF (30 mL) solution containing the residue was cooled to 0° C. and was mixed with tetrabutylammonium fluoride (1.0 mol/L THF solution, 2.66 mL, 2.66 mmol), followed by stirring for 15 hours. After the reaction mixture was distilled off under reduced pressure, the residue was purified by silica gel column chromatography (hexane/ethyl acetate=1/3) to obtain the compound (Z)-13-F (467 mg, 79%) as an oily substance.

$^1$H-NMR (CDCl$_3$, 400 MHz); δ2.56 (1H, d, J=9.2 Hz), 3.10 (1H, d, J=6.8 Hz), 7.57 (1H, d, J=10.0 Hz), 3.61 (1H, d, J=10.0 Hz), 4.04-4.08 (1H, m), 4.18-4.19 (1H, m) 、4.62 (2H, s) 、4.68-4.72 (1H, m), 4.76 (2H, t, J=4.8 Hz), 4.79 (2H, t, J=7.6 Hz), 4.95 (1H, d, J=7.2 Hz), 5.02 (1H, d, J=7.2 Hz), 7.04 (1H, dd, JC, F=78.8 Hz 、J=2.0 Hz).

(1S,2R,3R,4S, Z)-2-((Benzyloxy)methoxy)-1-(((benzyloxy)methoxy)methyl)-4-((tert-butyldimethylsilyl)oxy)-5-(fluoromethylene)-3-hydroxycyclopentane-1-carbonitrile (Compound (Z)-14-F) and its regioisomer (Compound (Z)-14'-F)

Next, a compound (Z)-14-F and its regioisomer compound (Z)-14'-F were synthesized as described below from the compound (Z)-13-F obtained in the aforementioned step.

[Chem. 36]

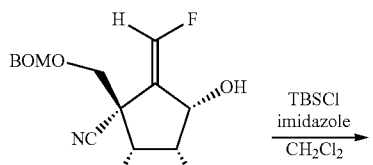
(Z)-13-F

TBSCl
imidazole
―――――――→
CH₂Cl₂

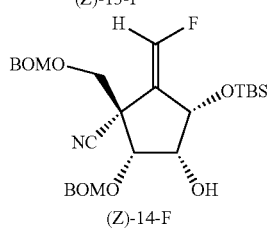
(Z)-14-F

+

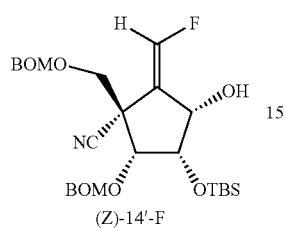
(Z)-14'-F

Specifically, in an argon gas flow at 0° C., t-butylchlorodimethylsilane (379 mg, 2.51 mmol) was added to a methylene chloride (20 mL) solution containing the compound (Z)-13-F (446 mg, 1.01 mmol) and imidazole (206 mg, 3.03 mmol), and the mixture was returned to room temperature and stirred for 96 hours. After methanol (1 mL) was added to the reaction solution, the mixture was partitioned between methylene chloride and an aqueous solution of saturated sodium hydrogen carbonate, and the organic layer was dried over anhydrous sodium sulfate.

After distillation under reduced pressure, the residue was purified by silica gel column chromatography (hexane/ethyl acetate=2/1) to obtain a mixture of the compound (Z)-14-F and its regioisomer compound (Z)-14'-F (510 mg, 91%, a mixing ratio of 3:2) as an oily substance.

$^1$H-NMR (CDCl$_3$, D2O, 400 MHz); δ0.145 (1.8H, s)、0.154 (3H、s)、0.17 (1.2H, s)、0.93 (5.4H, s)、0.95 (3.6H, s)、3.62 (0.4H, d、J=9.6 Hz), 3.63 (0.6H、d、J=9.6 Hz)、3.69 (1H, d, J=9.6 Hz), 3.98 (0.6H, t、J=4.4 Hz)、4.01 (0.6H, d, J=4.4 Hz), 4.11 (0.4H, dd、J=4.8 and 3.6 Hz), 4.15 (0.4H, d, J=4.8 Hz), 4.61-4.63 (2.4H, m), 4.70-4.79 (4.6H, m), 4.88-4.98 (2H, m)、6.96 (0.6H, dd, JC, F=80.0 Hz, J=1.6 Hz), 7.04 (0.4H, dd, JC, F=79.2 Hz, J=2.0 Hz)、7.29-7.38 (10H, m).

(1S,3R,5S,E)-5-((Benzyloxy)methoxy)-1-(((benzyloxy)methoxy)methyl)-3-((tert-butyldimethylsilyl)oxy)-2-(fluoromethylene)cyclopentane-1-carbonitrile (Compound (Z)-15-F)

Next, a compound (Z)-15-F was synthesized as described below from the compound (Z)-14-F and the compound (Z)-14'-F obtained in the aforementioned step.

[Chem. 37]

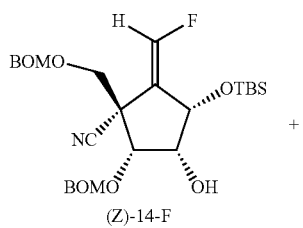
(Z)-14-F

+

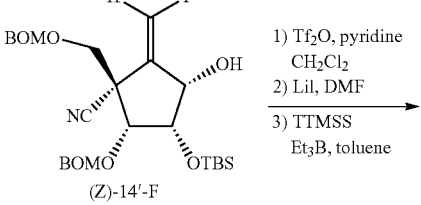
(Z)-14'-F

1) Tf₂O, pyridine
   CH₂Cl₂
2) LiI, DMF
―――――――→
3) TTMSS
   Et₃B, toluene

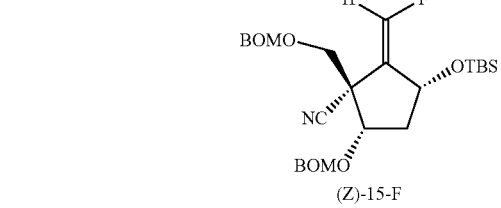
(Z)-15-F

Specifically, in an argon gas flow at 0° C., trifluoromethanesulfonic anhydride (303 μL, 1.8 mmol) was added dropwise to a methylene chloride (20 mL) solution containing the mixture of the compounds (Z)-14-F and (Z)-14'-F (500 mg, 0.9 mmol, the mixing ratio of 3:2) and pyridine (291 μL, 3.6 mmol), and the mixture was returned to room temperature and stirred for 40 minutes. The reaction solution was partitioned between methylene chloride and an aqueous solution of saturated sodium hydrogen carbonate, and the organic layer was dried over anhydrous sodium sulfate and distilled off under reduced pressure. The residue was mixed with DMF (13 mL) and lithium iodide (1.2 g, 9.0 mmol), followed by stirring under a light-shielded condition at room temperature for 22 hours. The reaction mixture was partitioned between an aqueous solution of saturated sodium hydrogen carbonate and ethyl acetate, and the organic layer was dried over anhydrous sodium sulfate and distilled off under reduced pressure. Tris(trimethylsilyl) silane (555 μL, 1.8 mmol) and triethylborane (1.0 mol/L THF solution, 900 μL, 0.9 mmol) were added to a toluene (18 mL) solution containing the residue, followed by stirring at room temperature for 30 minutes. The reaction solution was purified by silica gel column chromatography (hexane/ethyl acetate=6/1) to obtain the compound (Z)-15-F (262 mg, 54%) as an oily substance.

$^1$H-NMR (CDCl$_3$, 400 MHz); δ0.08 (3H, s), 0.09 (3H, s), 0.89 (9H, s), 1.98-2.05 (1H, m), 2.29-2.37 (1H, m), 3.57 (1H、d、J=10.0 Hz), 3.73 (1H、d、J=10.0 Hz), 4.00 (1H, t, J=6.8 Hz)、4.57-4.70 (4H, m)、4.79 (2H, s), 4.83-4.87 (3H, m)、6.92 (1H, dd, JC, F=80.4 Hz, J=2.0 Hz)、7.30-7.05 (10H, m).

(1S,3R,5S,Z)-5-((Benzyloxy)methoxy)-1-(((benzyloxy)methoxy)methyl)-2-(fluoromethylene)-3-hydroxycyclopentane-1-carbonitrile (Compound (Z)-16-F)

Next, a compound (Z)-16-F was synthesized as described below from the compound (Z)-15-F obtained in the aforementioned step.

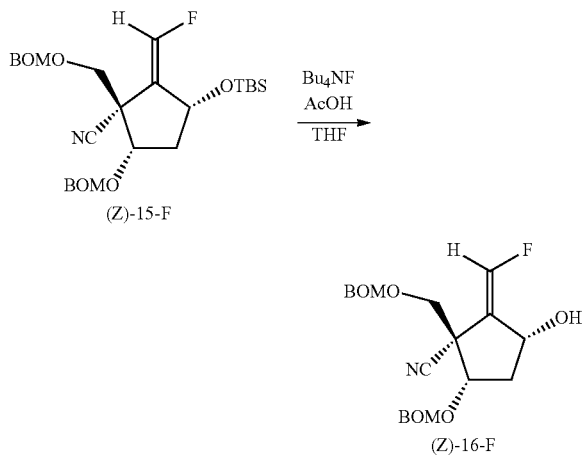

(Z)-15-F (Z)-16-F

Tetrabutylammoniumfluoride (1.0 mol/L THF solution, 960 μL, 0.96 mmol) was added to a THF (10 mL) solution containing the compound (Z)-15-F (260 mg, 0.48 mmol) and acetate (27 μL, 0.48 mmol), followed by stirring at room temperature 2 hours. After the reaction mixture was distilled off under reduced pressure, the residue was purified by silica gel column chromatography (hexane/ethyl acetate=1/2) to obtain the compound (Z)-16-F (170 mg, 83%) as an oily substance.

$^1$H-NMR (CDCl$_3$, 400 MHz); δ2.01-2.04 (2H, m), 2.56 (1H, d, J=8.8H z), 3.46 (1H, d, J=10.0 Hz), 3.51 (1H, d, J=10.0 Hz), 4.39-4.42 (1H, m), 4.60 (1H, d, J=12.0 Hz), 4.65 (1H, d, J=12.0 Hz), 4.69 (1H, d, J=12.0 Hz), 4.75 (1H, d, J=12.0 Hz), 4.79 (1H, d 、 J=8.8 Hz), 4.80 (1H, d 、 J=8.8 Hz), 4.90-4.94 (3H, m), 6.98 (1H, dd, JC, F=79.6 Hz, J=1.6H z) 、 7.29-7.39 (10H, m).

(1S,3S,5S,Z)-3-(2-Amino-6-oxo-1,6-dihydro-9H-purin-9-yl)-2-(fluoromethylene)-5-hydroxy-1-(hydroxymethyl)cyclopentane-1-carbonitrile (Compound (Z)-18-F)

Subsequently, as described below, a purine ring was added by a Mitsunobu reaction to the compound (Z)-16-F obtained in the aforementioned step to synthesize a compound (Z)-17-F, and then the protective group was removed from the obtained compound to obtain the compound (Z)-18-F.

[Chem. 39]

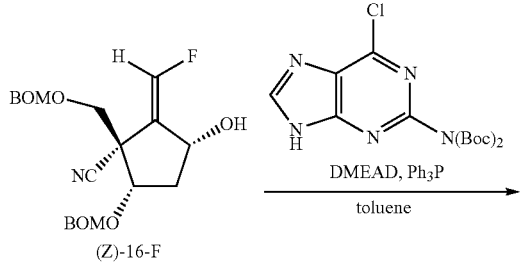

(Z)-16-F

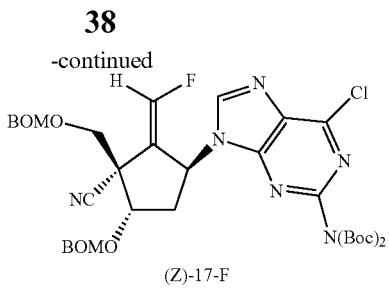

(Z)-17-F

Specifically, first, in an argon gas flow at −30° C., a toluene (4 mL) solution containing azodicarboxylic acid bis-(methoxyethyl) (230 mg, 0.98 mmol) was added dropwise to a toluene (4 mL) solution containing the compound (Z)-16-F (167 mg, 0.39 mmol), triphenylphosphine (257 mg, 0.98 mmol) and N2,N2-bis(t-butoxycarbonyl)-2-amino-6-chloropurine (362 mg, 0.98 mmol), followed by stirring for 4 hours. The reaction solution was partitioned between saturated saline and ethyl acetate, and the organic layer was dried over anhydrous sodium sulfate and then distilled off under reduced pressure. The residue was purified by silica gel column chromatography (hexane/ethyl acetate=2/1) to obtain the compound (Z)-17-F (267 mg, 88%) as a foam.

$^1$H-NMR (CDCl$_3$, 400 MHz); δ1.46 (18H, s) 、 2.54-2.57 (2H, m) 、 3.94 (1H, d, J=10.0 Hz), 4.13 (1H, d, J=10.0 Hz), 4.63-4.70 (4H, m, 4.76 (1H, d, J=11.6 Hz), 4.84 (2H, s), 4.90 (1H, d, J=11.2 Hz), 4.93 (1H, d, J=11.2 Hz), 5.78-5.82 (1H, m), 7.01 (1H, dd, JC, F=78.0 Hz, J=2.4 Hz) 、 7.27-7.36 (10H, m), 8.10 (1H, s).

[Chem. 40]

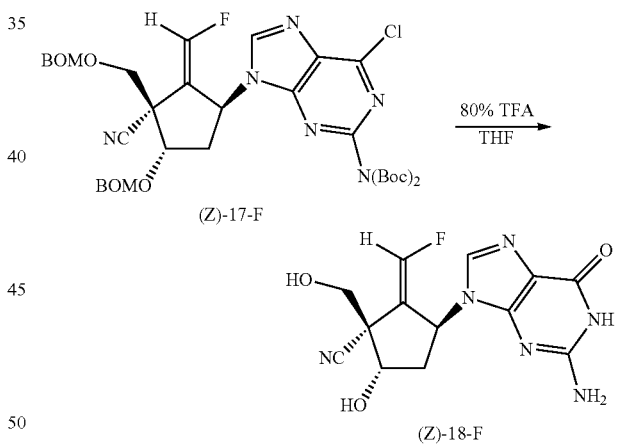

Next, 80% trifluoroacetate (12 mL) was added to a THF (3 mL) solution containing the compound (Z)-17-F (264 mg, 0.34 mmol), followed by stirring at room temperature for 72 hours. The reaction solution was distilled off under reduced pressure and thereafter azeotroped three times with ethanol (5 mL). Methanolic ammonia (saturated at 0° C., 5 mL) was added to the residue, and the mixture was stored at 4° C. for 14 hours. After the reaction solution was distilled off under reduced pressure, the residue was purified by reverse phase HPLC (30% methanol, 10 mL/min, a retention time of 9.92 minutes) to obtain the compound (Z)-18-F (47 mg, 43%) as a solid.

$^1$H NMR (DMSO-d6, 400 MHz) δ2.16-2.23 (1H, m), 2.27-2.33 (1H, m) 、 3.69 (1H, dd, J=11.2 and 6.0 Hz) 3.93 (1H, dd, J=11.2 and 5.6 Hz) 、 4.37-4.38 (1H, m), 5.63-5.67

(1H, m), 5.83 (1H, dd, J=6.0 and 5.6 Hz)、6.04 (1H, d, J=4.8 Hz), 6.41 (2H, br-s)、7.18 (1H, dd, JC, F=79.2 Hz, J=2.8 Hz)、7.70 (1H、s)、10.6 (1H、br-s).

Example 2

Moreover, a compound (compound (E)-18-Cl) represented by the following formula was synthesized by steps described below.

[Chem. 41]

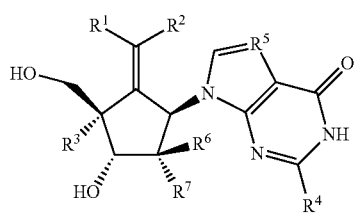

(1)

Note that the compound (E)-18-Cl is a compound represented by the above formula where $R^1$ is a chlorine atom, $R^2$ is a hydrogen atom, $R^3$ is a cyano group, $R^4$ is an amino group, $R^5$ is a nitrogen atom, $R^6$ is a hydrogen atom, and $R^7$ is a hydrogen atom. The compounds obtained in the following synthesis steps were each measured in terms of $^1$H nuclear magnetic resonance (NMR) spectrum, and ascertained to be a compound having a desired structure. The results of these measurements are presented below as well.

(3aS,4S,6S,7S,7aR,E)-8-(Chloromethylene)-6-methoxy-2,2-dimethyl-7-((trityloxy)methyl)tetrahydro-4H-4,7-methano[1,3]dioxolo[4,5-c]pyran (Compound (E)-10-Cl)

To begin with, a compound (E)-10-Cl was synthesized from the aforementioned compound (E)-9 as described below.

[Chem. 42]

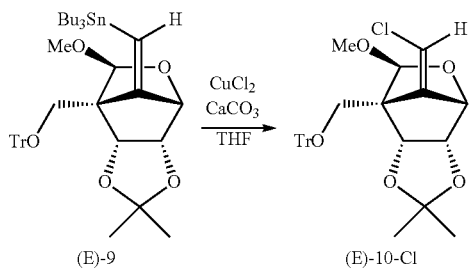

In an argon gas flow, copper (II) chloride (115 mg, 0.86 mmol) and calcium carbonate (171 mg, 1.71 mmol) were added to a THF (10 mL) solution containing the compound (E)-9 (220 mg, 0.29 mmol), and the mixture was stirred at room temperature for 22 hours under a condition light-shielded with aluminum foil. After the reaction mixture was partitioned between ethyl acetate and an aqueous solution of saturated sodium hydrogen carbonate, the organic layer was dried over anhydrous sodium sulfate. After the organic layer was distilled off under reduced pressure, the obtained residue was purified by silica gel column chromatography (hexane/ethyl acetate=2/1) to obtain the compound (E)-10-Cl (149 mg, 100%) as a solid.

$^1$H-NMR (CDCl$_3$, 400 MHz); δ1.40 (1H, s)、1.70 (3H, s)、3.41 (3H, s)、3.62 (1H, d、J=9.2 Hz)、3.79 (1H, d, J=9.2 Hz)、4.28 (1H, dd, J=2.2 and 7.8 Hz)、4.35 (1H, d, J=2.2 Hz)、4.55 (1H, d, J=7.8 Hz)、5.33 (1H, s)、6.0 (1H, s)、7.22-7.52 (15H, m).

(1S,2R,3R,4S,E)-4-(Acetoxymethyl)-4-cyano-5-(chloromethylene)cyclopentane-1,2,3-triyl triacetate (Compound (E)-10-Cl)

Next, a compound (E)-11-Cl was synthesized as described below from the compound (E)-10-Cl obtained in the aforementioned step.

[Chem. 43]

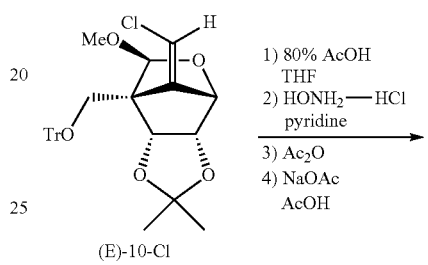

1) 80% AcOH THF
2) HONH$_2$—HCl pyridine
3) Ac$_2$O
4) NaOAc AcOH

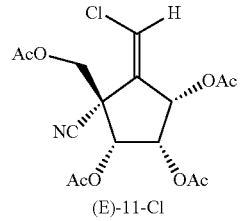

Specifically, 80% acetate (30 mL) was added to a THF (5 mL) solution containing the compound (E)-10-Cl (2.38 g, 4.58 mmol), followed by stirring at 80° C. for 6 hours. The reaction mixture was distilled off under reduced pressure, thereafter azeotroped three times with ethanol (20 mL), and dried under reduced pressure. The residue was mixed with pyridine (40 mL) and hydroxylamine hydrochloride (1.48 g, 22.9 mmol), followed by stirring at room temperature for 1 hour. Acetic anhydride (8.65 mL, 91.7 mmol) was added to the reaction mixture, followed by additional stirring for 12 hours. Methanol (10 mL) was added to the reaction solution, and the mixture was stirred for 10 minutes and then distilled off under reduced pressure. The residue was partitioned between an aqueous solution of saturated sodium hydrogen carbonate and chloroform, and the organic layer was dried over anhydrous sodium sulfate and then distilled off under reduced pressure. Sodium acetate (20 mg) and acetate (40 mL) were added to the residue, and the mixture was heated to 100° C. for 48 hours. The reaction solution was distilled off under reduced pressure, and then the residue was purified by silica gel column chromatography (hexane/ethyl acetate=1/1) to obtain the compound (E)-11-Cl (1.56 g, 88%) as a solid.

(5aS,7S,8R,8aR,E)-6-(Chloromethylene)-8-hydroxy-7-(hydroxymethyl)-2,2,4,4-tetraisopropyltetrahydro-6H-cyclopenta[f][1,3,5,2,4]trioxadisilepine-7-carbonitrile (Compound (E)-12-Cl)

Next, a compound (E)-12-Cl was synthesized as described below from the compound (E)-11-Cl obtained in the aforementioned step.

[Chem. 44]

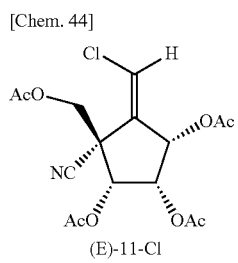

(E)-11-Cl

1) NH₃/MeOH
2) TIPDSCl₂ pyridine
→

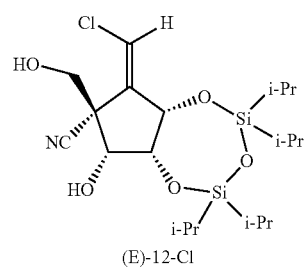

(E)-12-Cl

Methanolic ammonia (saturated at 0° C., 35 mL) was added to the compound (E)-11-Cl (1.33 g, 3.58 mmol) and the mixture was stored at 4° C. for 20 hours. The reaction solution was distilled off under reduced pressure and thereafter azeotroped three times with toluene (20 mL). The residue obtained by drying the resultant solution under reduced pressure for 24 hours by the vacuum pump was mixed with pyridine (36 mL), and the mixture was cooled to −30° C. in an argon gas flow. Then, 1,3-dichloro-1,1,3,3-tetraisopropyldisiloxane (1.24 mL, 3.94 mmol) was added dropwise to the reaction solution, followed by stirring at room temperature for 16 hours. Ethanol (10 mL) was added to the reaction solution, and the mixture was distilled off under reduced pressure. Thereafter, the residue was purified by silica gel column chromatography (hexane/ethyl acetate=5/7) to obtain the compound (E)-12-Cl (1.11 g, 69) as a solid.

¹H-NMR (CDCl₃, D₂O 、400 MHz); δ1.00-1.10 (28H, m) 、1.91 (1H, br-s) 、3.07 (1H, d, J=12.6 Hz) 、3.99-4.01 (1H, m) 、3.99-4.31 (1H, m) 、4.38 (1H, dd, J=12.6 and 3.2 Hz) 、4.44 (1H, dd, J=2.8 and 3.2 Hz) 、4.58 (1H, t, J=3.2 Hz) 、6.45 (1H, d, J=2.8 Hz).

(1S,2R,3S,4S,E)-2-((Benzyloxy)methoxy)-1-(((benzyloxy)methoxy)methyl)-5-(chloromethylene)-3,4-dihydroxycyclopentane-1-carbonitrile (Compound (E)-13-Cl)

Next, a compound (E)-13-Cl was synthesized as described below from the compound (E)-12-Cl obtained in the aforementioned step.

[Chem. 45]

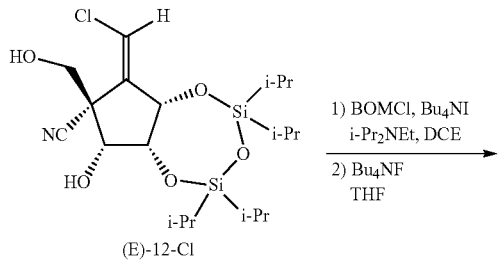

(E)-12-Cl

1) BOMCl, Bu₄NI i-Pr₂NEt, DCE
2) Bu₄NF THF
→

-continued

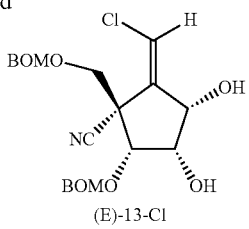

(E)-13-Cl

In an argon gas flow, a toluene (40 mL) solution containing the compound (E)-12-Cl (0.95 g, 2.05 mmol), benzyl chloromethyl ether (2.26 mL, 16.4 mmol), ethyldiisopropylamine (4.28 mL, 24.6 mmol), and tetrabutylammonium iodide (4.53 g, 12.3 mmol) was stirred at room temperature for 30 minutes, and then was heated and stirred at 80° C. for 23 hours. Methanol (5 mL) was added to the reaction solution, and the mixture was stirred at room temperature for 30 minutes, and thereafter was partitioned between ethyl acetate and an aqueous solution of saturated sodium hydrogen carbonate. The organic layer was dried over anhydrous sodium sulfate, and then distilled off under reduced pressure. Tetrabutylammonium fluoride (1.0 mol/L THF solution, 4.50 mL, 4.50 mmol) and acetate (0.12 mL, 2.05 mmol) were added to a THF (30 mL) solution containing the residue, followed by stirring for 19 hours. After the reaction mixture was distilled off under reduced pressure, the residue was purified by silica gel column chromatography (hexane/ethyl acetate=1/3) to obtain the compound (E)-13-Cl (969 mg, 100%) as an oily substance.

¹H-NMR (CDCl₃, 400 MHz); δ2.60 (1H, br-s) 、2.84 (1H, br-s) 、3.94 (1H, d, J=9.6 Hz) 、4.12 (1H, br-s) 、4.13 (1H, d, J=9.6 Hz) 、4.31 (1H, d, J=2.8 Hz) 、4.32 (1H, br-s) 、4.55 (2H, s) 、4.71-4.77 (4H, m) 、4.97 (2H, s) 、6.56 (1H, d, J=2.4 Hz) 、7.27-7.37 (10H, m).

(1S,2R,3R,4S,E)-2-((Benzyloxy)methoxy)-1-(((benzyloxy)methoxy)methyl)-4-((tert-butyldimethylsilyl)oxy)-5-(chloromethylene)-3-hydroxycyclopentane-1-carbonitrile (Compound (E)-14-Cl)

Next, a compound (E)-14-Cl was synthesized as described below from the compound (E)-13-Cl obtained in the aforementioned step.

[Chem. 46]

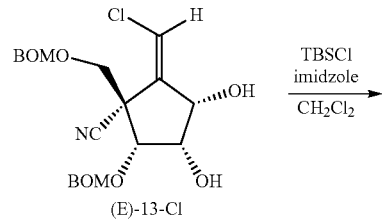

(E)-13-Cl

TBSCl imidzole
CH₂Cl₂
→

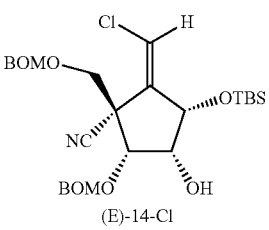

(E)-14-Cl

In an argon gas flow at 0° C., t-butylchlorodimethylsilane (648 mg, 4.30 mmol) was added to a methylene chloride (30 mL) solution containing the compound (E)-13-Cl (899 mg, 1.95 mmol) and imidazole (399 mg, 5.86 mmol), followed by stirring for 2 hours. Thereafter, the mixture was returned to room temperature and stirred for 45 hours. Methanol (5 mL) was added to the reaction solution, the mixture was stirred for 10 minutes and thereafter partitioned between methylene chloride and an aqueous solution of saturated sodium hydrogen carbonate, and the organic layer was dried over anhydrous sodium sulfate. After distillation under reduced pressure, the residue was purified by silica gel column chromatography (hexane/ethyl acetate=2/1) to obtain the compound (E)-14-Cl (864 mg, 77%) as an oily substance.

$^1$H-NMR (CDCl$_3$, 400 MHz); δ0.13 (3H, s) 、0.14 (3H, s) 、0.95 (9H, s) 、2.55 (1H, d, J=0.8 Hz) 、3.92 (1H, d, J=9.4 Hz) 、4.07 (1H, m) 、4.23 (1H, d, J=9.4 Hz) 、4.29 (1H, d, J=3.2 Hz) 、4.38 (1H, dd, J=2.4 and 2.8 Hz) 、4.54 (1H, s) 、4.55 (1H, s) 、4.72-4.80 (4H, m) 、5.00 (2H, s) 、6.33 (1H, d, J=2.4 Hz) 、7.27-7.38 (10H, m).

(1S,3R,5S,E)-5-((Benzyloxy)methoxy)-1-(((benzyloxy)methoxy)methyl)-3-((tert-butyldimethylsilyl)oxy)-2-(chloromethylene)cyclopentane-1-carbonitrile (Compound (E)-15-Cl)

Next, a compound (E)-15-Cl was synthesized as described below from the compound (E)-14-Cl obtained in the aforementioned step.

[Chem. 47]

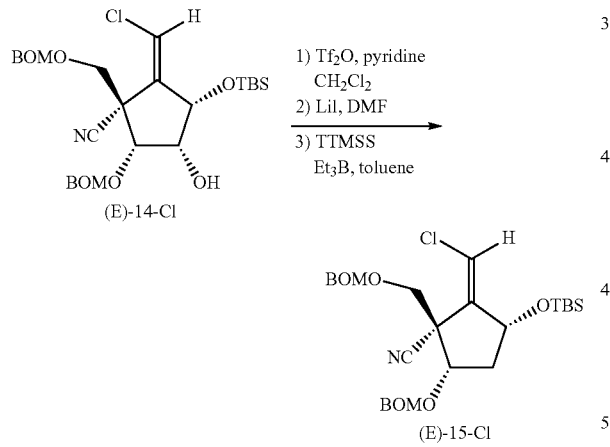

In an argon gas flow at 0° C., trifluoromethanesulfonic anhydride (455 μL, 2.78 mmol) was added dropwise to a methylene chloride (25 mL) solution containing the compound (E)-14-Cl (797 mg, 1.39 mmol) and pyridine (453 μL, 5.55 mmol), followed by stirring for 10 minutes. After that, the mixture was returned to room temperature and stirred for 20 minutes. The reaction solution was partitioned between methylene chloride and an aqueous solution of saturated sodium hydrogen carbonate, and the organic layer was dried over anhydrous sodium sulfate and distilled off under reduced pressure. DMF (25 mL) and lithium iodide (1.86 g, 13.9 mmol) were added to the residue, and the mixture was stirred at 0° C. for 10 minutes and then was further stirred at room temperature for 19 hours under a light-shielded condition. The reaction mixture was partitioned between saturated saline and ethyl acetate, and the organic layer was dried over anhydrous sodium sulfate and distilled off under reduced pressure. Tris(trimethylsilyl) silane (856 μL, 2.78 mmol) and triethylborane (1.0 mol/L THF solution, 1.39 mL, 1.39 mmol) were added to a toluene (10 mL) solution containing the residue, followed by stirring at room temperature for 1 hour. Thereafter, triethylborane (1.0 mol/L THF solution, 1.39 mL, 1.39 mmol) was added to the mixture, and the mixture was further stirred for 5 minutes. The reaction solution was partitioned between ethyl acetate and an aqueous solution of saturated sodium hydrogen carbonate, the organic layer was dried over anhydrous sodium sulfate and was distilled off under reduced pressure, and then the residue was purified by silica gel column chromatography (hexane/ethyl acetate=6/1) to obtain the compound (E)-15-Cl (485 mg, 62%) as an oily substance.

$^1$H-NMR (CDCl$_3$, 400 MHz); δ0.00 (3H, s) 、0.01 (3H, s) 、0.83 (9H, s) 、1.76-1.85 (1H, m) 、2.25-2.31 (1H, m) 、3.88 (1H, d, J=9.6 Hz) 、4.04 (1H, d, J=9.6 Hz) 、4.19 (1H, dd, J=11.2 and 6 Hz) 、4.25-4.30 (1H, m) 、4.49 (2H, s) 、4.61 (1H, s) 、4.62 (1H, s) 、4.66 (2H, s) 、4.81 (1H, d, J=16.6 Hz) 、4.84 (1H, d, J=16.6 Hz) 、6.27 (1H, d, J=2.4 Hz) 、7.22-7.23 (1H, m).

(1S,3R,5S,E)-5-((Benzyloxy)methoxy)-1-(((benzyloxy)methoxy)methyl)-2-(chloromethylene)-3-hydroxycyclopentane-1-carbonitrile (Compound (E)-16-Cl)

Next, a compound (E)-16-Cl was synthesized as described below from the compound (E)-15-Cl obtained in the aforementioned step.

[Chem. 48]

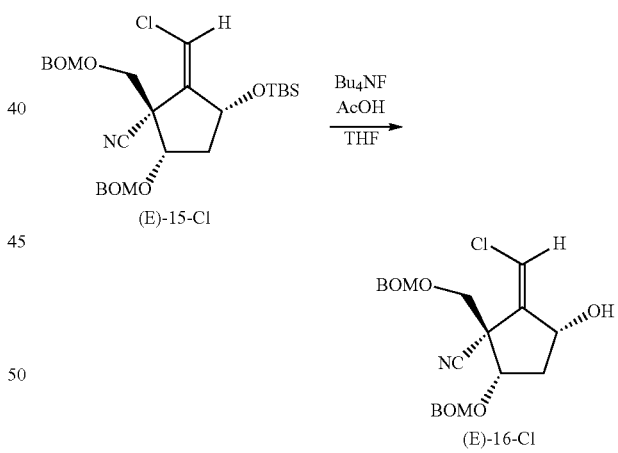

Tetrabutylammoniumfluoride (1.0 mol/L THF solution, 1.69 mL, 1.69 mmol) was added to a THF (10 mL) solution containing the compound (E)-15-Cl (472 mg, 0.85 mmol) and acetate (48 μL, 0.85 mmol), followed by stirring at room temperature for 30 minutes. After the reaction mixture was distilled off under reduced pressure, the residue was purified by silica gel column chromatography (hexane/ethyl acetate=1/1) and thereafter azeotroped twice with toluene (10 mL) to obtain the compound (E)-16-Cl (298 mg, 79%) as an oily substance.

$^1$H-NMR (CDCl$_3$, 400 MHz); δ2.01-2.07 (1H, m) 、2.09-2.20 (1H, m) 、2.69 (1H, d, J=11.2 Hz) 、3.52 (1H, d, J=10.0 Hz) 、4.07 (1H, d, J=10.0 Hz) 、4.56-4.59

(2H, m)、4.57 (1H, d, J=11.6 Hz)、4.64 (1H, d, J=11.6 Hz)、4.69 (1H, d, J=11.6 Hz)、4.75 (1H, d, J=11.6 Hz)、4.77 (1H, d, J=6.8 Hz)、4.89 (1H, d, J=6.8 Hz)、4.91 (1H, d, J=6.8 Hz)、4.96 (1H, d, J=6.8 Hz), 6.70 (1H, d, J=0.8 Hz)、7.30-7.40 (10H, m).

Subsequently, as described below, a purine ring was added by a Mitsunobu reaction to the compound (E)-16-Cl obtained in the aforementioned step to synthesize a compound (E)-17-Cl, and then the protective group was removed from the obtained compound to further obtain the compound (E)-18-Cl.

[Chem. 49]

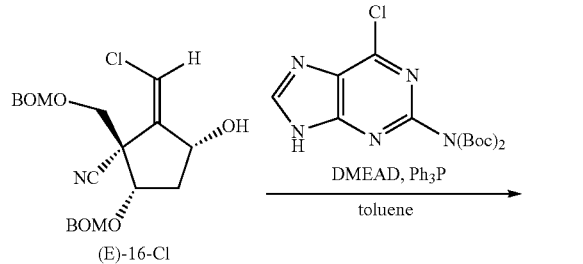

(E)-16-Cl

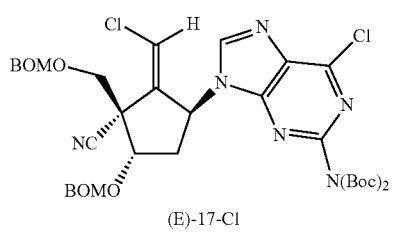

(E)-17-Cl

Specifically, first, in an argon gas flow at −30° C., a toluene (5 mL) solution containing azodicarboxylic acid bis-(methoxyethyl) (210 mg, 0.80 mmol) was added dropwise to a toluene (5 mL) solution containing the compound (E)-16-Cl (237 mg, 0.53 mmol), triphenylphosphine (187 mg, 0.80 mmol) and bi(Boc)-2-amino-6-chloropurine (296 mg, 0.80 mmol), followed by stirring for 10 minutes. Then, the reaction mixture was returned to room temperature and further stirred for 70 hours. The reaction solution was partitioned between saturated saline and ethyl acetate, and the organic layer was dried over anhydrous sodium sulfate, and then distilled off under reduced pressure. The residue was roughly purified by silica gel column chromatography (hexane/ethyl acetate=1/1) to obtain a mixture of the compound (E)-17-Cl and its regioisomer. The mixture was purified by HPLC (hexane/ethyl acetate=1/1, 20 mL/min, a retention time of 6.28 minutes) to obtain the compound (E)-17-Cl (312 mg, 58%) as a foam.

$^{1}$H-NMR (CDCl$_{3}$, 400 MHz); δ1.46 (18H, s)、2.39-2.45 (1H, m)、2.60-2.67 (1H, m)、4.14 (1H, d, J=10.4 Hz)、4.20 (1H, d, J=10.4 Hz)、4.58-4.64 (2H, m)、4.66 (1H, d, J=3.4 Hz)、4.69 (1H, d, J=3.4 Hz)、4.83 (1H, d, J=6.8 Hz)、4.86 (1H, d, J=6.8 Hz)、4.91 (1H, d, J=7.2 Hz)、4.96 (1H, d, J=7.2 Hz)、6.14 (1H, d, J=2.0 Hz)、7.28-7.40 (10H, m)、8.13 (1H, s).

(1S,3S,5S,E)-3-(2-Amino-6-oxo-1,6-dihydro-9H-purin-9-yl)-2-(fluoromethylene)-5-hydroxy-1-(hydroxymethyl)cyclopentane-1-carbonitrile (Compound (E)-18-Cl)

[Chem. 50]

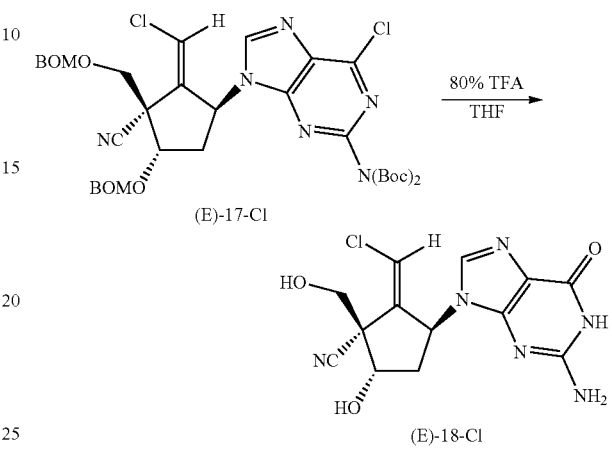

Next, 80% trifluoroacetate (35 mL) was added to a THF (2 mL) solution containing the compound (E)-17-Cl (168 mg, 0.21 mmol), followed by stirring at room temperature for 47 hours. The reaction solution was distilled off under reduced pressure and thereafter azeotroped five times with ethanol (75 mL). Methanolic ammonia (saturated at 0° C., 5 mL) was added to the residue, and the mixture was stored at 4° C. for 14 hours. The reaction solution was distilled off under reduced pressure, and then the residue was purified by reverse phase HPLC (5% methanol, 15 mL/min, a retention time of 9.19 minutes) to obtain the compound (E)-18-Cl (36 mg, 51%) as a solid.

$^{1}$H-NMR (DMSO-d6, 500 MHz) δ2.11-2.16 (1H, m)、2.56-2.64 (1H, m)、3.83 (1H, d, J=14.5 Hz)、3.96 (1H, d, J=14.5 Hz)、4.49 (1H, br-s)、5.51-5.56 (1H, m)、5.87 (1H, br-s)、6.13 (1H, br-s)、6.16 (1H, d, J=3.0 Hz)、6.44 (2H, br-s)、7.82 (1H, s)、10.61 (1H, s).

Subsequently, the nucleoside derivatives of the present invention were evaluated in terms of the antiviral activity and cytotoxicity in the following methods.

Test Example 1: Evaluation of Anti-HIV Activity

HIV-1 LAI was used as a wild-type HIV-1 molecular clone. In addition, MT-2 cells were used as cells to be infected. These cells were continuously cultured and maintained in a RPMI-1640 medium containing 10% FCS and supplemented with the aforementioned antibiotics. The MT-2 cells were exposed to HIV-1 LAI virus in an amount of 50 times the 50% infectious concentration (TCID 50), and the resultant MT-2 cells and a medium supplemented with each of the nucleoside derivatives at each of concentrations after serial dilution were together seeded into each cell of a 96-well cell culture dish at a concentration of 1×10$^{4}$ cells/mL. Then, after culturing for 7 days in the presence of each nucleoside derivative under standard culture conditions of 37° C. and 5% CO$_{2}$, the number of live cells in each well was quantified by MTT assay. Based on the numbers of live cells obtained, the EC$_{50}$ value was calculated and the anti- HIV activity of each nucleoside derivative was evaluated. The obtained results are presented in Table 1 and Table 2.

Test Example 2: Evaluation of Anti-HBV Activity

HepG2 2.2.15.7 cells were used as test cells. The HepG2 2.2.15.7 cells were prepared by using, as parent cell lines, HepG2 2.2.15 cells prepared so as to continuously produce HBV by introducing the HBV genes into human hepatoma cell lines (HepG2 cells). Meanwhile, the HepG2 2.2.15.7 cells were maintained by continuous culturing in DMEM containing 10% fetal calf serum, G418 (500 μg/ml), and antibiotics (penicillin and kanamycin).

The HepG2 2.2.15.7 cells are HBV continuously producing cells that carry not only genomically integrated DNAs, but also HBV genes produced as episomes. Therefore, the HepG2 2.2.15.7 cells were co-cultured with each nucleoside derivative, the DNA copy number of viruses released into the culture supernatant and the DNA copy number of the viruses present in the HepG2 2.2.15.7 cells were quantified, and a degree of decrease thereof was used as an index of the evaluation of the anti-HBV activity.

More specifically, the epG2 2.2.15.7 cells with a cell viability of 90% or more were seeded in a collagen-coated 96-well cell culture dish at a concentration of $2\times10^4$ cells/ml, and each nucleoside derivative was added at various concentrations at the same day as the cell seeding. After culturing for 3 days under the standard culture conditions of 37° C. and 5% $CO_2$, the medium was exchanged to a fresh medium containing each nucleoside derivative, and HBV DNA was collected from the culture supernatant on the third day after the exchange for a 1W assay (an assay on day 7 from the start of culture). In addition, a fresh medium containing each nucleoside derivative was further added to the cell plate after the collection of the supernatant, and the culture was further continued for 7 days. For a 2W assay (an assay on day 14 from the start of culture), intracellular HBV DNAs were collected from the HepG2 2.2.15.7 cells. Using these DNAs as a template, the quantitative PCR was performed to find the virus copy number from the calibration curve, and the 50% effect ($EC_{50}$) for each nucleoside derivative was calculated. The obtained results are presented in Table 1 and Table 2.

The DNA extractions from the supernatant of the HepG2 2.2.15.7 cells and from inside the cells were carried out using QIAamp Mini Elute virus Spin Kit (manufactured by QIAGEN), and 5 μL of the extracted DNAs was used for the qPCR. The PCR reaction was conducted by using a specific TaqMan probe primer, manufactured by Primer Design Ltd., which detects the HBV core protein region. The PCR reaction was carried out at 95° C. for 15 minutes, followed by 50 cycles of 95° C. for 10 seconds and 60° C. for 60 seconds. The obtained $C_T$ was converted to the HBV copy number using a calibration curve obtained from reactions in which HBV DNA fragments at a known concentration were diluted every 10-fold (from to $2\times10^8$ copies).

Test Example 3: Evaluation of Anti-HBV/Ce Activity

Regarding the above nucleoside derivatives, each nucleoside derivative was added to Huh-7 cells transfected with an ETV resistant strain (genotype: HBV/Ce, referred to as "HBV ETVr" in Table 1). After 72 hours from the addition, DNAs were extracted from the cells according to a conventional method, and analyzed by Southern blot using a probe for the HBV gene. Thus, the DNA copy number of the viruses was quantified, and the $EC_{50}$ value was calculated in the same way as described above. The obtained results are presented in Table 1.

Test Example 4: Cytotoxicity Test 1

The above nucleoside derivatives were also subjected to cytotoxicity tests on the MT-2 cells and HepG2 cells. Together with the medium to which each nucleoside derivative at each concentration after serial dilution was added, the MT-2 cells were seeded at a concentration of $1\times10^4$, whereas the HepG2 cells were seeded at a concentration of $1\times10^4$. Thus, these cells were cultured in the presence of each nucleoside derivative at various concentrations for 7 days under the standard culture conditions of 37° C. and 5% $CO_2$, and thereafter the number of live cells in each well was quantified by an MTT assay. Based on the numbers of live cells obtained, the $CC_{50}$ was calculated for each nucleoside derivative. The obtained results are presented in Table 1 and Table 2.

Test Example 5: Cytotoxicity Test 2

PXB cells were used as test cells. PXB cells were fresh human hepatocytes isolated from chimeric mice with humanized liver and were maintained in a dHCGM medium for PXB cells. Both the cells and the medium are made by PhoenixBio Co., Ltd.

The PXB cells were seeded at $3\times10^5$ cells/ml on a collagen-coated 96-well plate and cultured together with each compound at each concentration after stepwise dilution for 7 days under the standard culture conditions of 37° C. and 5% $CO_2$, and thereafter the number of live cells in each well was quantified by an MTT assay. Based on the obtained values, the degree of cytotoxicity was determined, and the $CC_{50}$ value was calculated as the cytotoxicity of each compound. The obtained results are presented in Table 1.

TABLE 1

| Structural formula | Antiviral activity, $EC_{50}$ (μM) | | | Cytotoxicity, $CC_{50}$ (μM) | | |
|---|---|---|---|---|---|---|
| | HIV-1 | HBV | HBV ETVr | MT-2 | HepG2 | PXB |
| [structure] | 0.02 | 1W assay:0.003<br>2W assay:0.007 | 0.0653 | >100 | 50 | >100 |

TABLE 2

| Structural formula | Antiviral activity, $EC_{50}$ (μM) | | Cytotoxicity, $CC_{50}$ (μM) | |
|---|---|---|---|---|
| | HIV-1 | HBV | MT-2 | HepG2 |
| (structure: cyclopentane with HOCH₂, =CH₂, NC, HO substituents and guanine base) | 0.16 | 2W assay:0.03 | >100 | 89 |
| (structure: cyclopentane with HOCH₂, =CH₂, H₂O, HO substituents and guanine base) | >1 | 2W assay:0.01 | >100 | 67 |
| (structure: cyclopentane with HOCH₂, =CH₂, F, HO substituents and guanine base) | >1 | 2W assay:0.09 | >100 | >100 |
| (structure: cyclopentane with HOCH₂, =CH₂, vinyl, HO substituents and guanine base) | >1 | 2W assay:>1 | >100 | >100 |
| (structure: cyclopentane with HOCH₂, =CH₂, ethynyl, HO substituents and guanine base) | 0.027 | 2W assay:>1 | >100 | >100 |

As is apparent from the results presented in Table 1, the nucleoside derivatives of the present invention exhibited an excellent antiviral activity against HBV. Furthermore, it was revealed that the nucleoside derivatives also exhibited an antiviral activity against HBV resistant to entecavir which is an existing nucleoside derivative. It was also found that the nucleoside derivatives also had an antiviral activity against HIV. On the other hand, the toxicity of the nucleoside derivatives to the host cells of the virus was low.

Similarly, it was also found that the nucleoside derivative of the present invention presented in Table 2 had an antiviral activity, and also had the low toxicity to host cells of the virus.

INDUSTRIAL APPLICABILITY

As described above, according to the present invention, it is possible to provide a nucleoside derivative having excellent antiviral activities against HBV and HIV and having low toxicity to host cells. In addition, the nucleoside derivative can exert an antiviral activity against HBV resistant to an existing nucleoside derivative. Therefore, the present invention is very useful in prophylaxes and therapies of viral infections.

The invention claimed is:
1. A nucleoside derivative represented by the following general formula:

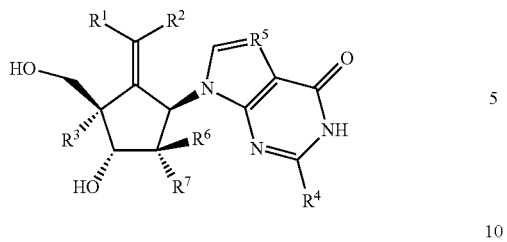

in the formula, $R^1$ represents a hydrogen or halogen atom, $R^2$ represents a hydrogen or halogen atom, $R^3$ represents a cyano group, an alkyl group which may have a substituent, an alkenyl group which may have a substituent, an alkynyl group which may have a substituent, a halogen atom, or an azido group, $R^4$ represents an amino group, a hydrogen atom, a halogen atom, or a hydroxy group, $R^5$ represents a nitrogen atom or a methine group, $R^6$ represents a hydrogen atom or a hydroxy group, and $R^7$ represents a hydrogen atom or a hydroxy group.

2. The nucleoside derivative according to claim 1, wherein, in the formula, $R^3$ is a cyano group.

3. The nucleoside derivative according to claim 1, wherein, in the formula, $R^1$ is a halogen atom and $R^2$ is a hydrogen atom, or $R^1$ is a hydrogen atom and $R^2$ is a halogen atom.

4. The nucleoside derivative according to claim 2, wherein, in the formula, $R^1$ is a halogen atom and $R^2$ is a hydrogen atom, or $R^1$ is a hydrogen atom and $R^2$ is a halogen atom.

5. An antiviral agent comprising the nucleoside derivative according to claim 1 as an active ingredient.

* * * * *